(12) United States Patent
Mulder et al.

(10) Patent No.: US 9,974,815 B2
(45) Date of Patent: May 22, 2018

(54) COMPOSITIONS COMPRISING BACTERIAL STRAINS

(71) Applicant: 4D Pharma Research Limited, Aberdeen (GB)

(72) Inventors: Imke Elisabeth Mulder, Aberdeen (GB); Amy Beth Holt, Aberdeen (GB); Domenico Panzica, Aberdeen (GB); Seanin Marie McClusky, Aberdeen (GB)

(73) Assignee: 4D Pharma Research Limited (GB)

( * ) Notice: Subject to any disclaimer, the term of this patent is extended or adjusted under 35 U.S.C. 154(b) by 0 days. days.

(21) Appl. No.: 15/803,723

(22) Filed: Nov. 3, 2017

(65) Prior Publication Data

US 2018/0055892 A1    Mar. 1, 2018

Related U.S. Application Data

(62) Division of application No. 15/357,850, filed on Nov. 21, 2016, now Pat. No. 9,839,558.

(30) Foreign Application Priority Data

Nov. 20, 2015  (GB) ................................. 1520502.4
Mar. 23, 2016  (GB) ................................. 1604924.9

(51) Int. Cl.
| A61K 35/74 | (2015.01) |
| A61K 31/739 | (2006.01) |
| A23C 9/158 | (2006.01) |
| A61K 45/06 | (2006.01) |
| A61K 39/09 | (2006.01) |
| A23L 33/135 | (2016.01) |
| A61K 9/19 | (2006.01) |
| A61K 39/00 | (2006.01) |
| A61K 35/00 | (2006.01) |

(52) U.S. Cl.
CPC ............ *A61K 35/74* (2013.01); *A23C 9/1585* (2013.01); *A23L 33/135* (2016.08); *A61K 9/19* (2013.01); *A61K 31/739* (2013.01); *A61K 39/09* (2013.01); *A61K 45/06* (2013.01); *A23V 2002/00* (2013.01); *A61K 2035/11* (2013.01); *A61K 2039/585* (2013.01)

(58) Field of Classification Search
CPC ............ A61K 2300/00; A61K 31/4375; A61K 31/444; A61K 31/4545; A61K 31/4709; A61K 31/496; A61K 31/506; A61K 38/12; C07D 455/02
See application file for complete search history.

(56) References Cited

U.S. PATENT DOCUMENTS

| 5,589,168 | A  | 12/1996 | Allen et al. |
| 7,749,494 | B2 | 7/2010  | Renaud et al. |
| 7,998,474 | B2 | 8/2011  | Kelly |
| 8,460,648 | B2 | 6/2013  | Borody |
| 9,011,834 | B1 | 4/2015  | McKenzie et al. |
| 9,314,489 | B2 | 4/2016  | Kelly et al. |
| 9,539,293 | B2 | 1/2017  | Kelly et al. |
| 9,662,381 | B2 | 5/2017  | Honda et al. |
| 9,796,762 | B2 | 10/2017 | Kelly et al. |
| 9,808,519 | B2 | 11/2017 | Honda et al. |
| 9,839,655 | B2 * | 12/2017 | Mulder ................. A61K 35/74 |
| 2003/0147858 | A1 | 8/2003 | Renaud et al. |
| 2008/0069861 | A1 | 3/2008 | Brown et al. |
| 2010/0284973 | A1 | 11/2010 | Schiffer-Mannioui et al. |
| 2010/0303782 | A1 | 12/2010 | Cobb et al. |
| 2010/0311686 | A1 | 12/2010 | Kasper et al. |
| 2010/0316617 | A1 | 12/2010 | Renaud et al. |
| 2014/0037716 | A1 | 2/2014 | Nowill et al. |
| 2014/0147425 | A1 | 5/2014 | Henn et al. |
| 2014/0154218 | A1 | 6/2014 | Kohno et al. |
| 2014/0199281 | A1 | 7/2014 | Henn et al. |
| 2014/0335131 | A1 | 11/2014 | Mazmanian et al. |
| 2014/0341921 | A1 | 11/2014 | Honda et al. |
| 2015/0071957 | A1 | 3/2015 | Kelly et al. |
| 2015/0104418 | A1 | 4/2015 | Flint et al. |
| 2016/0067188 | A1 | 3/2016 | Cade et al. |
| 2016/0199424 | A1 | 7/2016 | Berry et al. |
| 2016/0279177 | A1 | 9/2016 | Kelly et al. |
| 2017/0143772 | A1 | 5/2017 | Mulder et al. |
| 2017/0143773 | A1 | 5/2017 | Mulder et al. |
| 2017/0143774 | A1 | 5/2017 | Mulder et al. |
| 2017/0143775 | A1 | 5/2017 | Mulder et al. |
| 2017/0173089 | A1 | 6/2017 | Kelly |
| 2017/0319634 | A1 | 11/2017 | Grant et al. |
| 2017/0326184 | A1 | 11/2017 | Patterson et al. |
| 2017/0326202 | A1 | 11/2017 | Kelly |
| 2017/0354695 | A1 | 12/2017 | Grant et al. |

FOREIGN PATENT DOCUMENTS

| CN | 101590081 A | 12/2009 |
| CN | 102940652 A | 2/2013 |
| CN | 103156888 A | 6/2013 |
| CN | 103981115 A | 8/2014 |
| CN | 102940652 B | 3/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |

(Continued)

OTHER PUBLICATIONS

Atarashi, et al., Treg induction by a rationally selected mixture of Clostridia strains from the human microbiota.Supplementary Information. Nature 500, 232-236 (Aug. 8, 2013) doi:10.1038/nature12331.

(Continued)

*Primary Examiner* — Padmavathi Baskar

(74) *Attorney, Agent, or Firm* — Wilson Sonsini Goodrich & Rosati

(57) ABSTRACT

The invention provides compositions comprising bacterial strains for treating and preventing cancer.

10 Claims, 7 Drawing Sheets

(56) References Cited

FOREIGN PATENT DOCUMENTS

| | | |
|---|---|---|
| CN | 104546942 A | 4/2015 |
| EP | 1448995 A1 | 8/2004 |
| EP | 2687227 A1 | 1/2014 |
| EP | 2810652 A2 | 12/2014 |
| EP | 2832859 A1 | 2/2015 |
| JP | H08259450 A | 10/1996 |
| JP | 2003261453 A | 9/2003 |
| JP | 2005097280 A | 4/2005 |
| JP | 2007084533 A | 4/2007 |
| JP | 2007116991 A | 5/2007 |
| JP | 2009507023 A | 2/2009 |
| JP | 2013527240 A | 6/2013 |
| JP | 2015500792 A | 1/2015 |
| KR | 20100128168 A | 12/2010 |
| WO | WO-9919459 A1 | 4/1999 |
| WO | WO-03046580 A1 | 6/2003 |
| WO | WO-2007027761 A2 | 3/2007 |
| WO | WO-2007136719 A2 | 11/2007 |
| WO | WO-2009027753 A1 | 3/2009 |
| WO | WO-2009072889 A1 | 6/2009 |
| WO | WO-2011110918 A1 | 9/2011 |
| WO | WO-2011149335 A1 | 12/2011 |
| WO | WO-2011152566 A2 | 12/2011 |
| WO | WO-2011153226 A2 | 12/2011 |
| WO | WO-2011153226 A3 | 3/2012 |
| WO | WO-2013008039 A2 | 1/2013 |
| WO | WO-2013050792 A1 | 4/2013 |
| WO | WO-2013080561 A1 | 6/2013 |
| WO | WO-2014001368 A1 | 1/2014 |
| WO | WO-2014067976 A1 | 5/2014 |
| WO | WO-2014075745 A1 | 5/2014 |
| WO | WO-2014078911 A1 | 5/2014 |
| WO | WO-2014121298 A2 | 8/2014 |
| WO | WO-2014121304 A1 | 8/2014 |
| WO | WO-2014137211 A1 | 9/2014 |
| WO | WO-2014145958 A2 | 9/2014 |
| WO | WO-2014167338 A1 | 10/2014 |
| WO | WO-2014201037 A2 | 12/2014 |
| WO | WO-2015006355 A2 | 1/2015 |
| WO | WO-2015013214 A2 | 1/2015 |
| WO | WO-2015021936 A1 | 2/2015 |
| WO | WO-2015095241 A2 | 6/2015 |
| WO | WO-2015156419 A1 | 10/2015 |
| WO | WO-2015156519 A1 | 10/2015 |
| WO | WO-2015169944 A1 | 11/2015 |
| WO | WO-2016019506 A1 | 2/2016 |
| WO | WO-2016102950 A1 | 6/2016 |
| WO | WO-2016102951 A1 | 6/2016 |

OTHER PUBLICATIONS

Cekanaviciute, et al., Gut bacteria from multiple sclerosis patients modulate human T cells and exacerbate symptoms in mouse models. PNAS. Jun. 30, 2017; 1-6.
Colowick, S. and Kaplan, N., Methods of Enzymology. Academic Press, Inc.
Co-pending U.S. Appl. No. 15/842,635, filed Dec. 14, 2017.
Kogyo, S. Lactic Acid Bacteria, Intestinal Flora ad Health II; Physiological effects of heat-treated lactococcus "EF-2001" and application to food. Mar. 30, 2001, vol. 44, No. 6, pp. 35-39.
Narushima, et al., Characterization of the 17 strains of regulatory T cell-inducing human-derived Clostridia. Gut Microbes Mar. 18, 2014; 5:3, 333-339.
Office Action dated Jan. 2, 2018 for U.S. Appl. No. 15/357,936.
Office Action dated Dec. 6, 2017 for U.S. Appl. No. 15/592,178.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.

"Amedei, A. et al. Multiple sclerosis: the role of cytokines in pathogenesis and in therapies. Int J Mol Sci. Oct. 19, 2012;13(10):13438-60. doi: 10.3390/ijms131013438."
Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.
Atarashi et al., Th17 Cell Induction by Adhesion of Microbes to Intestinal Epithelial Cells. Cell, vol. 163, No. 2, Oct. 8, 2015. pp. 367-380.
Atarashi, K. et al., Treg induction by a rationally selected mixture of Clostridia strains from the human microbiota. Nature. 2013; 500(7461):232-236.
Atlas, R. Handbook of Microbiological Media, Fourth Edition. CRC Press. 2010.
Ausubel, et al. Current Protocols in Molecular Biology. 1987. Supplement 30.
Ausubel et al., Short protocols in molecular biology. Fifth edition, 2002.
Azad, M.B. et al., Probiotic supplementation during pregnancy or infancy for the prevention of asthma and wheeze: systematic review and meta-analysis BMJ 2013; 347 :f6471.
Bagge, et al., Diversity of spore-forming bacteria in cattle manure, slaughterhouse waste and samples from biogas plants. Journal of applied microbiology. 2010;109: 1549-1565.
Balato, et al., Effects of adalimumab therapy in adult subjects with moderate-to-severe psoriasis on Th17 pathway. (2014) J Eur Acad Dermatol Venereol. 28(8):1016-24.
Bertram, J. et al. Establishment of a cloned line of Lewis lung carcinoma cells adapted to cell culture. (1980) Cancer let. 11:63-73.
Birdi, K.S. Handbook of Surface and Colloid Chemistry, 2nd Edition. CRC Press. 1997.
Bottacini, et al., Comparative genomics of the Bifidobacterium brevetaxon. BMC Genomics, 2014; 15:170. DOI:10.1186/1471-1471-2164-15-170.
Brand et al., Collagen-induced arthritis, 2007; Protocol 2(5):1269-1275.
Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.
"Campeau, J.L. et al., Intestinal Epithelial Cells Modulate Antigen-Presenting Cell Responses to Bacterial DNA. Infectionand Immunity. Aug. 2012; 80(8): 2632-2644."
Caspi, P.R. Experimental autoimmune uveoretinitis in the rat and mouse. Curr Protoc Immunol. May 2003 ;Chapter 15:Unit 15.6. doi: 10.1002/0471142735.im1506s53.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chen, S. et al., Live combined bacillus subtilis and enterococcus faecium ameliorate murine experimental colitis by immunosuppression. International journal of inflammation. 2014(878054). 7 Pages.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.
Chiu, et al., Monocolonization of germ-free mice with bacteroides fragilis protects against dectran sulfate sodium-induced acute colitis. Biomed Research International 2014. vol. 2014. Article ID 675786. 9 Pages.
Collins, M.D., et al., *Enterococcus avium* nom. rev., comb. nov.; *E. casseliflavus* nom. rev., comb. nov.; *E. durans* nom. rev., comb. nov.; *E. gallinarum* comb. nov.; and *E. malodoratus* sp. nov. (1984) Int J Syst Evol Microbiol. 34: 220-223.
Co-pending U.S. Appl. No. 15/359,144, filed Nov. 22, 2016.
Co-pending U.S. Appl. No. 15/673,270, filed Aug. 9, 2017.
Co-pending U.S. Appl. No. 15/679,857, filed Aug. 17, 2017.
Co-pending U.S. Appl. No. 15/700,007, filed Sep. 8, 2017.
Co-pending U.S. Appl. No. 15/704,245, filed Sep. 14, 2017.
Co-pending U.S. Appl. No. 15/803,721, filed Nov. 3, 2017.

(56) References Cited

OTHER PUBLICATIONS

Dahya V. et al., Clostridium ramosum Osteomyelitis in an immunocompetent patient after traumatic injury, Infectious Diseases in Clinical Practice Mar. 12, 2015 Lippincott Williams and Wilkins USA, vol. 23, No. 2, Mar. 12, 2015, pp. 102-104, XP009193312, ISSN: 1056-9103 the whole document.
Darlington, G.J., Liver Cell Lines. (1987) Meth Enzymol. 151:19-38.
Day, J.G. et al., Cryopreservation and Freeze-Drying Protocols. Springer. 2007. 2nd edition.
Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.
Duncan et al. (2002) "*Roseburia* intestinal is sp. nov., a novel saccharolytic, butyrate-producing bacterium from human faeces," International Journal System Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.
Eckburg, PB. et al., Diversity of the human intestinal microbial flora.Science. Jun. 10, 2005;308(5728):1635-8. Epub Apr. 14, 2005.
Fabro, A. et al., The Th17 pathway in the peripheral lung microenvironment interacts with expression of collagen V in the late state of experimental pulmonary fibrosis. (2015) Immunobiology. 220(1):124-35.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Fenner, et al., *Bacteroides massiliensis* sp. nov., isolated from blood culture of a newborn. International Journal of systematic and evolutionary microbiology, 2005. 55: 1335-1337.
Frank, D. et al., Molecular-phylogenetic characterization of microbial community imbalances in human inflammatory bowel diseases. 2007. PNAS. 104(34):13780-5.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.
GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
Gennaro, A.R., Remington's Pharmaceutical sciences, Mack publishin co. 1985.
Gennaro, A.R., Remington: The Science and practice of pharmacy. 20th edition. 2000.
Ghadimi, D. et al., Epigenetic imprinting by commensal probiotics inhibits the IL-23/IL-17 axis in an in vitro model of the intestinal mucosal immune system. JLB. 2012;92(4):895-911.
Goldin, B.R. et al., Clinical indications for probiotics: an overview. Clin Infect Dis. Feb. 1, 2008;46 Suppl 2:S96-100; discussion S144-51. doi: 10.1086/523333.
Guide for the care and use of laboratory animals: 8th edition. The national academic press; 2011.
Haabeth et al. A model for cancer-suppressive inflammation. (2012) OncoImmunology 1(1):1146-1152.
Hammerich, L. et al., Interleukins in chronic liver disease: lessons learned from experimental mouse models. (2014) Clin Exp Gastroenterol. 7:297-306.
Holdeman, et al., *Eubacterium contortum* (Prevot) comb. nov.: Emendation of description and designation of the type strain. International journal of systematic bacteriology. Oct. 1971;21(4): 304-306.
Hougee, et al., Oral treatment with probiotics reduces allergic symptoms in ovalbumin-sensitized mice:a bacterial strain comparative study. Int Arch Allergy Immunol. 2010; 151:107-117.
International Search Report dated Jan. 27, 2017 for International Application No. PCT/GB2016/053622.
International Search Report dated Feb. 17, 2017 for International Application No. PCT/GB2016/053676.
International Search Report dated Aug. 26, 2016 for International application No. PCT/GB2016/051774.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
Ispirli, H. et al., Characterization of functional properties of Enterococcus faecium strains isolated from human gut.Can. J. Microbial. 61: 861-870 (2015) dx.doi.org/10.1139/cjm-2015-0446.
Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jiao et al., Blockade of Notch Signaling Ameliorates Murine Collagen-Induced Arthritis via Suppressing Th1 and Th17 Cell Responses. 2014; Pathology, 184(4):1085-1091.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. S1912.
Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79.
Karin, M. Nuclear factor-kappaB in cancer development and progression. Nature. May 25, 2006;441(7092):431-6.
Kitahara, M. et al., *Bacteroides plebeius* sp. nov. and *Bacteroides coprocola* sp. nov., isolated from human faeces. International journal of systematic and evolutionary microbiology. 2005; 55: 2143-2147.
Koenders, M.I. et al., Interleukin-17 Acts Independently of TNF-a under Arthritic Conditions. (2006) J. Immunol. 176:6262-6269.

(56) References Cited

OTHER PUBLICATIONS

Kverka, M. et al., Oral administration of Parabacteroides distasonis antigens attenuates experimental murine colitis through modulation of immunity and microbiota composition. Clinical & Experimental Immunology. 2010; 163:250-259.
Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9. 2015.
Lejeune, FJ. et al., Efficiency of Recombinant Human TNF in Human Cancer Therapy. (2006) Cancer Immun. 6:6.
Leslie, et al., Trehalose and sucrose protect both membranes and proteins in intact bacteria during drying. (1995) Appl. Environ. Microbiol. 61, 3592-3597.
Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages.
Luger, D. and Caspi, R.R., New perspectives on effector mechanisms in uveitis. (2008) Semin. Immunopathol. 30(2): 134-143.
Lyons, et al., Bacterial strain-specific induction of Foxp3 T regulatory cells is protective in murine allergy models. Clinical & Experimental Allergy. 2010; 40:811-819.
Machiels, K. A decrease of the butyrate-producing species *Roseburia hominis* and *Faecalibacterium prausnitzii* defines dysbiosis in patients with ulcerative colitis.Gut. Aug. 2014;63(8):1275-83. doi: 10.1136/gutjnl-2013-304833. Epub Sep. 10, 2013.
Macpherson, AJ. et al., IgA responses in the intestinal mucosa against pathogenic and non-pathogenic microorganisms. Oct. 2001. 3(12). 1021-1035.
Macpherson, AJ., et al., The functions of mucosal T cells in containing the indigenous commensal flora of the intestine.Cell Mol Life Sci. Dec. 2002;59(12):2088-96.
Macsharry et al., Immunomodulatory effects of feeding with bifidobacterium longum on allergen-induced lung inflammation in the mouse. Pulmonary pharmacology & Therapeutics. 2012; 25:325-334.
Manni et al., A tale of two cytokines: IL-17 and IL-22 in asthma and infection. Expert Rev Respir Med. Feb. 2014 ; 8(1): 25-42. doi:10.1586/17476348.2014.854167.
Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.
Masco, L., et al., Identification of Bifidobacterium Species Using rep-PCR Fingerprinting. Systematic and Applied Microbiology 26(4):557-63 • Dec. 2003.
Maya, J.R. et al., Emerging Therapies for Noninfectious Uveitis: What May Be Coming to the Clinics. (2014) J. Ophthalmology. 310329.
Mazmanian, SK., An immunomodulatory molecule of symbiotic bacteria directs maturation of the host immune system.Cell. Jul. 15, 2005;122(1):107-18.
Miossec et al., Targeting IL-17 and TH17 cells in chronic inflammation, 2012; Nature Drug Discovery 11, 763-776.
Miossec, P. et al. Targeting IL-17 and TH17 cells in chronic inflammation. Nat Rev Drug Discov. Oct. 2012;11(10):763-76. doi: 10.1038/nrd3794.
Mitropoulou, G. et al. Immobilization Technologies in Probiotic Food Production. (2013) Journal Nutr Metab. (2013) 716861.
Miyake, et al., Phylogenetic analysis of the genus bifidobacterium and related genera based on 16S rDNA sequences. Microbiol. Immunol. 1998; 42(10): 661-667.
Miyake, T. et al., Phylogenetic Analysis of the Genus Bifidobacterium and Related Genera Based on 16S rDNA Sequences. Microbiol. Immunol. 1998; 42(10):661-667.
Miyamoto-Shinohara, Y. et al., Survival of freeze-dried bacteria. J Gen Appl Microbiol. Feb. 2008;54(1):9-24.
Miyauchi, E., Control of multiple sclerosis by gut microbiota. Journal of clinical and experimental medicine. 2015. vol. 253 No. 5.2, pp. 445-450.
Monteleone, I. et al., Th17-related cytokines: new players in the control of chronic intestinal inflammation. (2011) BMC Medicine. 2011, 9:122.
Mucientes, A. et al., Specific association of IL17A genetic variants with panuveitis. (2015) Br J Ophthalmol. 99(4):566-70.
Mukai et al., SH3BP2 Gain-Of-Function Mutation Exacerbates Inflammation and Bone Loss in a Murine Collagen-Induced Arthritis Model, 2014 PLoS ONE 9(8): e105518.
Notice of allowance dated Sep. 1, 2017 for U.S. Appl. No. 15/357,850.
Notice of Allowance dated Nov. 22, 2017 for U.S. Appl. No. 15/359,988.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 13, 2012 for U.S. Appl. No. 12/760,926.
Office Action dated Dec. 19, 2005 for U.S. Appl.No. 10/275,706.
Overstreet et al. 'Dysbiosis Characterized by Reduced Abundance of Roseburia is Associated With Increased Severity of Colitis in IL-10-/-Mice'. Gastroenterology. 2011, vol. 140, No. 5, Suppl. 1, pp. S-696.
Pace et al. Macrophage activiation: Priming activity from a T-cell hybridoma is attributable to interferon. (1983) PNAS. 80:3782-6.
Parabacteroides distasonis (Eggerth and Gagnon) Sakamoto and Benno (ATCC 8503). Sep. 19, 2017. 2 Pages.
Park, S.K. et al., *Blautia stercoris* sp. nov., isolated from human faeces. International journal of systematic and evolutionary microbiology. 2012; 62(4): 776-779.
Patel., R. et al., Determination of 16S rRNA sequences of enterococci and application to species identification of nonmotile enterococcus gallinarum isolates. Journal of clinical microbiology, 1998; 36(11):3399-3407.
Rockwell, S.C. et al., Characteristics of a Serially Transplanted Mouse Mammary Tumor and Its Tissue-Culture-Adapted Derivative. (1972) J Natl Cancer Inst. 49:735-49.

(56) References Cited

OTHER PUBLICATIONS

Sagar, et al., Bifidobacterium breve and lactobacillus rhamnosus treatment is as effective as budesonide at reducing inflammation in a murine model for chronic asthma. Respiratory Research. 2014; 15(46):1-17.
Sakamoto, M. et al., Reclassification of Bacteroides distasonis, Bacteroides goldsteinii and Bacteroides merdae as *Parabacteroides distasonis* gen. nov., comb. nov., *Parabacteroides goldsteinii* comb. nov. and *Parabacteroides merdae* comb. nov. International journal of systematic and evolutionary microbiology. 2006; 56: 1599-1605.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Scher et al., Expansion of intestinal Prevotella copri correlates with enhanced susceptibility to arthritis. 2013; eLIFE 2, e01202, 20 Pages.
Schieck, M. et al., Genetic variation in TH17 pathway genes, childhood asthma, and total serum IgE levels.(2014) J Allergy Clin Immunol. 133(3):888-91.
Schleifer, K.H. et al., Transfer of *Streptococcus faecalis* and *Streptococcus faecium* to the Genus *Enterococcus* nom. rev. as *Enterococcus faecalis* comb. nov. and *Enterococcus faecium* comb. nov. Int J Syst Evol Microbiol, Jan. 1984 34: 31-34, doi:10.1099/00207713-34-1-31.
Schmitz, S. et al., A prospective, randomized, blinded, placebo-controlled pilot study on the effect of Enterococcus faecium on clinical activity and intestinal gene expression in canine food—responsive chronic enteropathy. J Vet Intern Med. Mar.-Apr. 2015;29(2):533-43. doi: 10.1111/jvim.12563. Epub Mar. 16, 2015.
Schouten, et al., Cow milk allergy symptoms are reduced in mice fed dietary synbiotics during oral sensitization with whey. Nutritional Immunology. 2015; 139(7):1390-403.
Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.
Severijnen, et al., Chronic Arthritis Induced in Rats by Cell Wall Fragments of *Eubacterium* Species from the Human Intestinal Flora. Infection and Immunity, Feb. 1990; 58(2): p. 523-528.
Sgadari, C. et al., Interferon-inducible protein-10 identified as a mediator of tumor necrosis in vivo. (1996) PNAS. 93:13791-6.
Sgadari et al. Mig, the Monokine Induced by Interferon-g, Promotes Tumor Necrosis In Vivo. (1997) Blood. 89:2635-43.
Shabgah, A.G. et al., Interleukin-17 in human inflammatory diseases. Postepy Dermatol Alergol. Aug. 2014; 31(4): 256-261.
Simpson-Herren, L. et al., Kinetic parameters and growth curves for experimental tumor systems. Cancer Chemother Rep. Jun. 1970;54(3):143-74.
Sisson, G. et al., Randomised clinical trial: a liquid multi-strain probiotic vs. placebo in the irritable bowel syndrome—a 12 week double-blind study. Aliment Pharmacol Ther. 2014; 40: 51-62.
Sivieri, K. et al., Probiotic enterococcus faecium CRL 183 inhibit chemically induced colon cancer in male wistar rats. Eur Food Res Technol. 2008; 228:231-237.
Smith, T.F. et al., Comparison of biosequences. (1981) Adv. Appl. Math. 2: 482-489.
Song et al., Impact of Schistosoma japonicum Infection on Collagen-Induced Arthritis in DBA/1 Mice: A Murine Model of Human Rheumatoid Arthritis. 2011; PLoS ONE 6, e23453, 10 pages.
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. *longum* and *Bifidobacterium longum* ssp. *infantis* strains of human origin.J Microbiol Methods. Oct. 2011;87(1):10-6. doi: 10.1016/j.mimet.2011.06.014. Epub Jul. 2, 2011.

Stoll et al., Altered microbiota associated with abnormal humoral immune responses to commensal organisms in enthesitis-related arthritis, 2014; Arthritis Res Ther. 16:486.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strobel, H.J. Basic laboratory culture methods for anaerobic bacteria. Methods Mol Biol. 2009;581:247-61. doi: 10.1007/978-1-60761-214-8_16.
Sun, D. et al., The role of Th17-associated cytokines in the pathogenesis of experimental autoimmune uveitis (EAU). (2015) Cytokine. 74(1):76-80.
Tanaka, K. and Watanabe, K., In Vitro tebipenem activity against anaerobic bacteria. Japanese Journal of Chemotherapy. Mar. 2009. vol. 57 S-1.
Tesmer, LA. et al., Th17 cells in human disease. Immunol Rev. 2008;223:87-113.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.
Tsukinowa, et al., Fecal microbiota of a dugong (Dugong dugong) in captivity at Toba Aquarium. J. Gen. Appl. Microbiol., 54, 25-38 (2008).
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
Van De Veerdonk, et al., The Anti-CD20 antibody rituximab reduces the Th17 cell response. Arthritis & Rheumatism. Jun. 2011; 63(6):1507-1516.
Vetrovsky, T. and Baldrian, P., The variability of the 16S rRNA gene in bacterial genomes and its consequences for bacterial community analyses. Plos One. Feb. 2013; 8(2): e57923.
Workman et al. Guidelines for the welfare and use of animals in cancer research (2010) Br. J. Cancer. 102:1555-77.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.
Ye, X. et al., The Role of IL-23/Th17 Pathway in Patients with Primary Immune Thrombocytopenia. (2015) PLoS One. 10(1):e0117704.
Yin, X. et al., Combined effect of five single nucleotide polymorphisms related to IL23/Th17 pathway in the risk of psoriasis.Immunogenetics. Mar. 2014;66(3):215-8. doi: 10.1007/s00251-013-0756-z. Epub Jan. 14, 2014.
Yutin, N. and Galperin, M.Y., A genomic update on clostridial phylogeny:Gram-negative spore formers and other misplaced clostridia. Environmental microbiology. 20136; 15(10): 2631-2641.
Zhang, B. et al., Oral administration of enterococcus faecalis FK-23 suppresses Th17 cell development and attenuates allergic airway responses in mice. International journal of molecular medicine. 2012; 30:248-254.
Zhang, B. et al., The Prevalence of Th17 Cells in Patients With Gastric Cancer. 2008. Biochem Biophys Res Commun 374 (3), 533-537.
Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.
Zheng, B. et al., Bifidobacteriu breve attenuates murine dextran sodium sulfate-induced colitis and increases regulatory T cell responses. PLOS one. May 2014; 9(5).
Zhongyuan, T. et al., The inflammation regulation effects of enterococcus faecium HDRsEf1 on human enterocyte-like HT-29 cells. Animal cells and systems. Mar. 2016;20(2):70-76.

(56) References Cited

OTHER PUBLICATIONS

Zhu, S. and Qian, Y., IL-17/IL-17 receptor system in autoimmune disease: mechanisms and therapeutic potential. Clinical Science (2012) 122, 487-511.
Zitomersky, N. et al., Characterization of Adherent Bacteroidales from Intestinal Biopsies of Children and Young Adults with Inflammatory Bowel Disease. PLOS one. 2013; 8(6).
Zitvogel, et al., Type I interferons in anticancer immunity. Nature Reviews. Jul. 2015:405-414.

* cited by examiner

Negative control

Positive Control

Addition of MRX518

Addition of MRX518 and LPS

Negative control (No bacteria)

Negative Control (Bacterial sediment)

Addition of MRX518

COMPOSITIONS COMPRISING BACTERIAL STRAINS

CROSS REFERENCE

This application is a divisional of U.S. application Ser. No. 15/357,850, filed on Nov. 21, 2016; which claims priority to GB Application No. 1604924.9, filed on Mar. 23, 2016, and to GB Application No. 1520502.4, filed on Nov. 20, 2015, both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Nov. 18, 2016, is named 49455-709-201_P067592XX_sequence_listing.txt and is 3,999,976 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 500-1000 different phylotypes belonging essentially to two major bacterial divisions, the Bacteroidetes and the Firmicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host. Similarly, the immunological importance of the gut microbiota is well-recognized and is exemplified in germ-free animals which have an impaired immune system that is functionally reconstituted following the introduction of commensal bacteria [3-5].

Dramatic changes in microbiota composition have been documented in gastrointestinal disorders such as inflammatory bowel disease (IBD). For example, the levels of *Clostridium* cluster XIVa bacteria are reduced in subjects with IBD whilst numbers of *E. coli* are increased, suggesting a shift in the balance of symbionts and pathobionts within the gut [6-9]. Interestingly, this microbial dysbiosis is also associated with imbalances in T effector cell populations.

In recognition of the potential positive effect that certain bacterial strains may have on the animal gut, various strains have been proposed for use in the treatment of various diseases (see, for example, [10-13]). Also, certain strains, including mostly *Lactobacillus* and *Bifidobacterium* strains, have been proposed for use in treating various inflammatory and autoimmune diseases that are not directly linked to the intestines (see [14] and [15] for reviews). However, the relationship between different diseases and different bacterial strains, and the precise effects of particular bacterial strains on the gut and at a systemic level and on any particular types of diseases, are poorly characterized. For example, certain *Enterococcus* species have been implicated in causing cancer [16].

There is a requirement in the art for new methods of treating diseases. There is also a requirement for the potential effects of gut bacteria to be characterized so that new therapies using gut bacteria can be developed.

SUMMARY OF THE INVENTION

The inventors have developed new therapies for treating and preventing diseases. In particular, the inventors have developed new therapies for treating and preventing cancer. In particular, the inventors have identified that bacterial strains of the species *Enterococcus gallinarum* can be effective for treating and preventing cancer. As described in the examples, oral administration of compositions comprising *Enterococcus gallinarum* may reduce tumor size in mouse models of cancer.

In preferred embodiments, the invention provides a composition comprising a bacterial strain of the species *Enterococcus gallinarum*, for use in a method of treating or preventing cancer, such as breast, lung or liver cancer. The inventors have identified that treatment with compositions comprising a bacterial strain of the species *Enterococcus gallinarum* can reduce tumor growth in mouse models of breast, lung and liver cancer. In certain embodiments, the composition is for use in a method of reducing tumor size or preventing tumor growth in the treatment of cancer. Compositions using *Enterococcus gallinarum* may be particularly effective for reducing tumor size or preventing tumor growth in the treatment of cancer.

In preferred embodiments of the invention, the bacterial strain in the composition is of *Enterococcus gallinarum*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Enterococcus gallinarum*. Preferably, the bacterial strain has a 16s rRNA sequence that is at least 95%, 96%, 97%, 98%, 99%, 99.5% or 99.9% identical to SEQ ID NO:1 or 2. Preferably, the sequence identity is to SEQ ID NO:2. Preferably, the bacterial strain for use in the invention has the 16s rRNA sequence represented by SEQ ID NO:2.

Accordingly, the invention also provides a composition comprising a bacterial strain that has a 16s rRNA sequence that is at least 95% identical to the 16s rRNA sequence of a bacterial strain of *Enterococcus gallinarum* for use in a method of treating or preventing cancer. In particular, the invention provides a composition comprising a bacterial strain that has a 16s rRNA sequence that is at least 95% identical to SEQ ID NO: 2 for use in a method of treating or preventing cancer. In some embodiments, the bacterial strain in the composition is not of *Enterococcus gallinarum*. In some embodiments, the bacterial strain in the composition is not of *Enterococcus gallinarum*, but is a closely related strain.

In certain embodiments, the composition of the invention is for oral administration. Oral administration of the strains of the invention can be effective for treating cancer. Also, oral administration is convenient for patients and practitioners and allows delivery to and/or partial or total colonization of the intestine.

In certain embodiments, the composition of the invention comprises one or more pharmaceutically acceptable excipients or carriers.

In certain embodiments, the composition of the invention comprises a bacterial strain that has been lyophilized. Lyophilization is an effective and convenient technique for preparing stable compositions that allow delivery of bacteria.

In certain embodiments, the composition comprises a lyoprotectant which is a pharmaceutically acceptable excipient, diluent, or carrier.

In certain embodiments, the composition comprises a bacterial strain that has been lyophilized; and further comprises a pharmaceutically acceptable excipient, diluent, or carrier.

In certain embodiments, the composition is a lyophilized composition. In some cases, the lyophilized composition may be reconstituted prior to administration to a subject. In some cases, the reconstitution is with a diluent described herein. In some cases, the diluent may be sterile water, sodium chloride solution, or dextrose solution.

In certain embodiments, the invention provides a food product comprising the composition as described above.

In certain embodiments, the invention provides a vaccine composition comprising the composition as described above.

Additionally, the invention provides a method of treating or preventing cancer, comprising administering a composition comprising a bacterial strain of the species *Enterococcus gallinarum*.

In developing the above invention, the inventors have identified and characterized a bacterial strain that is particularly useful for therapy. The *Enterococcus gallinarum* strain of the invention is shown to be effective for treating cancer. Therefore, in another aspect, the invention provides a cell of the *Enterococcus gallinarum* strain deposited under accession number NCIMB 42488, or a derivative thereof. The invention also provides compositions comprising such cells, or biologically pure cultures of such cells. The invention also provides a cell of the *Enterococcus gallinarum* strain deposited under accession number NCIMB 42488, or a derivative thereof, for use in therapy, in particular for cancer. Similarly, the invention provides a cell of a bacterial strain that has a 16s rRNA sequence that is at least 95% identical to SEQ ID NO: 2, or a derivative thereof. The invention also provides compositions comprising such cells, or biologically pure cultures of such cells. The invention also provides a cell of a bacterial strain that has a 16s rRNA sequence that is at least 95% identical to SEQ ID NO:2, or a derivative thereof, for use in therapy, in particular for treating or preventing cancer.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference.

DETAILED DESCRIPTION

Bacterial Strains

Figure 1:
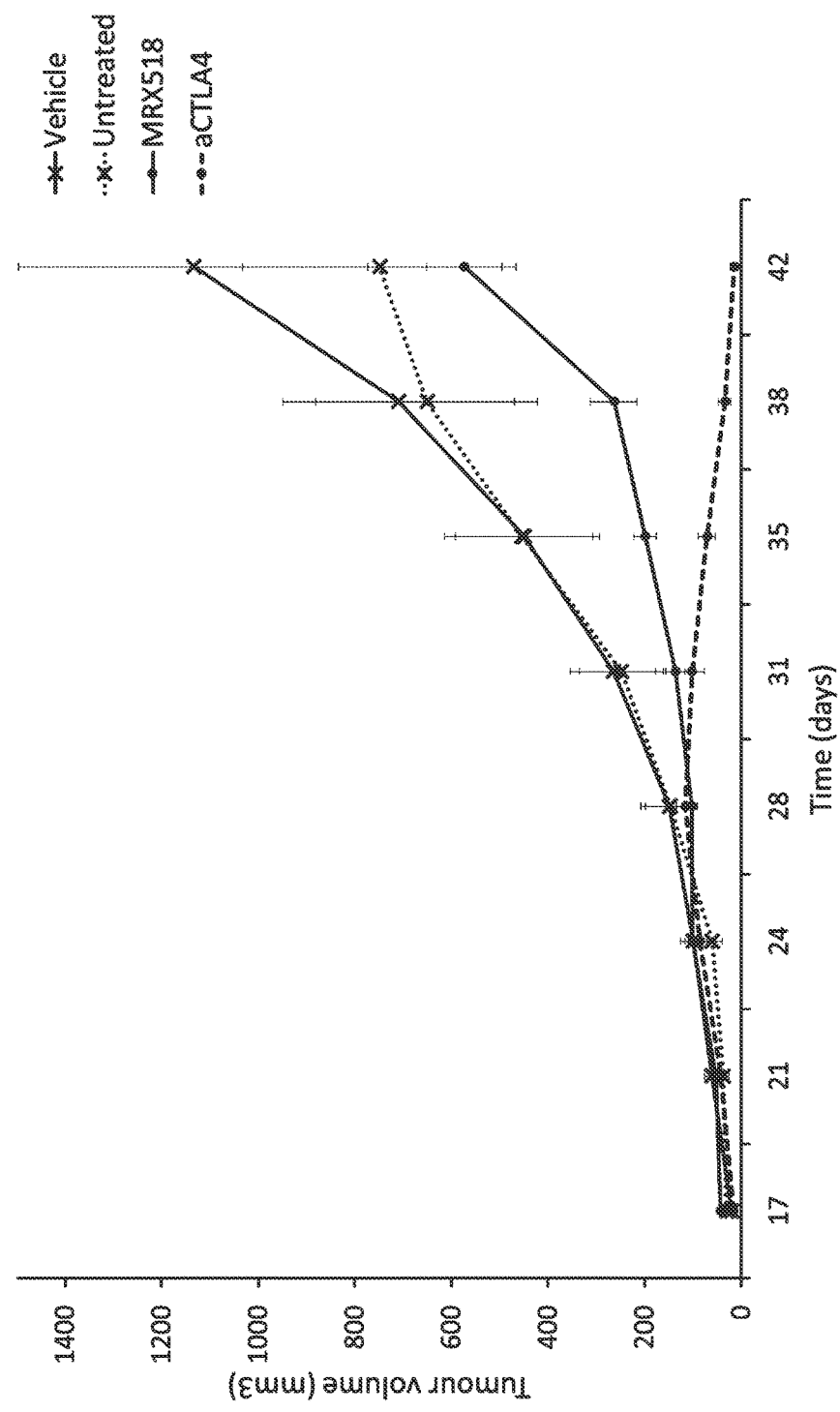
FIG. 1: Mouse model of breast cancer—tumor volume.

The compositions of the invention comprise a bacterial strain of the species *Enterococcus gallinarum*. The examples demonstrate that bacteria of this species are useful for treating or preventing cancer.

The invention also provides compositions comprising a bacterial strain that has a 16s rRNA sequence that is at least 95% identical to the 16s rRNA sequence of a bacterial strain of *Enterococcus gallinarum* for use in therapy, for example, for use in a method of treating or preventing cancer. In particular, the invention also provides compositions comprising a bacterial strain that has a 16s rRNA sequence that is at least 95% identical to SEQ ID NO: 2 for use in therapy, for example, for use in a method of treating or preventing cancer. In some embodiments, the bacterial strain in the composition is not of *Enterococcus gallinarum*, but is a closely related strain.

The invention provides an *Enterococcus gallinarum* for use in therapy, for example, for use in treating or preventing cancer. Similarly, the invention provides a composition comprising a bacterial strain of the species *Enterococcus gallinarum*, for use in therapy, for example, for use in treating or preventing cancer. In certain embodiments, the compositions of the invention comprise a bacterial strain that has a 16s rRNA sequence that is at least 95% identical to SEQ ID NO: 2, for example which is a *Enterococcus gallinarum*, and do not contain any other bacterial genus. In certain embodiments, the compositions of the invention comprise a single strain of a bacterial strain that has a 16s rRNA sequence that is at least 95% identical to SEQ ID NO: 2, for example, which is an *Enterococcus gallinarum*, and do not contain any other bacterial strain or species.

*Enterococcus gallinarum* forms coccoid cells, mostly in pairs or short chains. It is nonmotile and colonies on blood agar or nutrient agar are circular and smooth. *Enterococcus gallinarum* reacts with Lancefield group D antisera. The type strain of *Enterococcus gallinarum* is F87/276=PB21=ATCC 49573=CCUG 18658=CIP 103013=JCM 8728=LMG 13129=NBRC 100675=NCIMB 702313 (formerly NCDO 2313)=NCTC 12359 [17]. The GenBank accession number for a 16S rRNA gene sequence of *Enterococcus gallinarum* is AF039900 (disclosed herein as SEQ ID NO:1). An exemplary *Enterococcus gallinarum* strain is described in [17].

All microorganism deposits were made under the terms of the Budapest Treaty. Maintenance of a viable culture is assured for 30 years from the date of deposit. All restrictions on the availability to the public of the deposited microorganisms will be irrevocably removed upon the granting of a patent for this application. The *Enterococcus gallinarum* bacterium deposited under accession number NCIMB 42488 was tested in the Examples and is also referred to herein as strain MRX518. References to MRX518 and MRx0518 are used interchangeably. A 16S rRNA sequence for the MRX518 strain that was tested is provided in SEQ ID NO:2. Strain MRX518 was deposited with the international depositary authority NCIMB, Ltd. (Ferguson Building, Aberdeen, AB21 9YA, Scotland) by 4D Pharma Research Ltd. (Life Sciences Innovation Building, Aberdeen, AB25 2ZS, Scotland) on 16 Nov. 2015 as "*Enterococcus sp*" and was assigned accession number NCIMB 42488.

The genome of strain MRX518 comprises a chromosome and plasmid. A chromosome sequence for strain MRX518 is provided in SEQ ID NO:3. A plasmid sequence for strain MRX518 is provided in SEQ ID NO:4. These sequences were generated using the PacBio RS II platform.

Bacterial strains closely related to the strain tested in the examples are also expected to be effective for treating or preventing cancer. In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Enterococcus gallinarum*. Preferably, the bacterial strain for use in the invention has a 16s rRNA sequence that is at least 95%, 96%, 97%, 98%, 99%, 99.5% or 99.9% identical to SEQ ID NO:1 or 2. Preferably, the sequence identity is to SEQ ID NO:2. Preferably, the bacterial strain for use in the invention has the 16s rRNA sequence represented by SEQ ID NO:2.

Bacterial strains that are biotypes of the bacterium deposited under accession number 42488 are also expected to be effective for treating or preventing cancer. A biotype is a closely related strain that has the same or very similar physiological and biochemical characteristics.

Strains that are biotypes of the bacterium deposited under accession number NCIMB 42488 and that are suitable for use in the invention may be identified by sequencing other nucleotide sequences for the bacterium deposited under accession number NCIMB 42488. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, (GTG)$_5$, or REP or [18]. Biotype strains may have sequences with at least 95%, 96%, 97%, 98%, 99%, 99.5% or 99.9% sequence identity to the corresponding sequence of the bacterium deposited under accession number NCIMB 42488. In some embodiments, a biotype strain has a sequence with at least 95%, 96%, 97%, 98%, 99%, 99.5% or 99.9% sequence identity to the corresponding sequence of strain MRX518 deposited as NCIMB 42488 and comprises a 16S rRNA sequence that is at least 99% identical (e.g. at least 99.5% or at least 99.9% identical) to SEQ ID NO:2. In some embodiments, a biotype strain has a sequence with at least 95%, 96%, 97%, 98%, 99%, 99.5% or 99.9% sequence identity to the corresponding sequence of strain MRX518 deposited as NCIMB 42488 and has the 16S rRNA sequence of SEQ ID NO:2.

In certain embodiments, the bacterial strain for use in the invention has a chromosome with sequence identity to SEQ ID NO:3. In preferred embodiments, the bacterial strain for use in the invention has a chromosome with at least 90% sequence identity (e.g. at least 92%, 94%, 95%, 96%, 97%, 98%, 99% or 100% sequence identity) to SEQ ID NO:3 across at least 60% (e.g. at least 65%, 70%, 75%, 80%, 85%, 95%, 96%, 97%, 98%, 99% or 100%) of SEQ ID NO:3. For example, the bacterial strain for use in the invention may have a chromosome with at least 90% sequence identity to SEQ ID NO:3 across 70% of SEQ ID NO:3, or at least 90% sequence identity to SEQ ID NO:3 across 80% of SEQ ID NO:3, or at least 90% sequence identity to SEQ ID NO:3 across 90% of SEQ ID NO:3, or at least 90% sequence identity to SEQ ID NO:3 across 100% of SEQ ID NO:3, or at least 95% sequence identity to SEQ ID NO:3 across 70% of SEQ ID NO:3, or at least 95% sequence identity to SEQ ID NO:3 across 80% of SEQ ID NO:3, or at least 95% sequence identity to SEQ ID NO:3 across 90% of SEQ ID NO:3, or at least 95% sequence identity to SEQ ID NO:3 across 100% of SEQ ID NO:3, or at least 98% sequence identity to SEQ ID NO:3 across 70% of SEQ ID NO:3, or at least 98% sequence identity to SEQ ID NO:3 across 80% of SEQ ID NO:3, or at least 98% sequence identity to SEQ ID NO:3 across 90% of SEQ ID NO:3, or at least 98% identity to SEQ ID NO:3 across 95% of SEQ ID NO:3, or at least 98% sequence identity to SEQ ID NO:3 across 100% of SEQ ID NO:3, or at least 99.5% sequence identity to SEQ ID NO:3 across 90% of SEQ ID NO:3, or at least 99.5% identity to SEQ ID NO:3 across 95% of SEQ ID NO:3, or at least 99.5% identity to SEQ ID NO:3 across 98% of SEQ ID NO:3, or at least 99.5% sequence identity to SEQ ID NO:3 across 100% of SEQ ID NO:3.

In certain embodiments, the bacterial strain for use in the invention has a plasmid with sequence identity to SEQ ID NO:4. In preferred embodiments, the bacterial strain for use in the invention has a plasmid with at least 90% sequence identity (e.g. at least 92%, 94%, 95%, 96%, 97%, 98%, 99% or 100% sequence identity) to SEQ ID NO:4 across at least 60% (e.g. at least 65%, 70%, 75%, 80%, 85%, 95%, 96%, 97%, 98%, 99% or 100%) of SEQ ID NO:4. For example, the bacterial strain for use in the invention may have a plasmid with at least 90% sequence identity to SEQ ID NO:4 across 70% of SEQ ID NO:4, or at least 90% sequence identity to SEQ ID NO:4 across 80% of SEQ ID NO:4, or at least 90% sequence identity to SEQ ID NO:4 across 90% of SEQ ID NO:4, or at least 90% sequence identity to SEQ ID NO:4 across 100% of SEQ ID NO:4, or at least 95% sequence identity to SEQ ID NO:4 across 70% of SEQ ID NO:4, or at least 95% sequence identity to SEQ ID NO:4 across 80% of SEQ ID NO:4, or at least 95% sequence identity to SEQ ID NO:4 across 90% of SEQ ID NO:4, or at least 95% sequence identity to SEQ ID NO:4 across 100% of SEQ ID NO:4, or at least 98% sequence identity to SEQ ID NO:4 across 70% of SEQ ID NO:4, or at least 98% sequence identity to SEQ ID NO:4 across 80% of SEQ ID NO:4, or at least 98% sequence identity to SEQ ID NO:4 across 90% of SEQ ID NO:4, or at least 98% sequence identity to SEQ ID NO:4 across 100% of SEQ ID NO:4.

In certain embodiments, the bacterial strain for use in the invention has a chromosome with sequence identity to SEQ ID NO:3 and a plasmid with sequence identity to SEQ ID NO:4.

In certain embodiments, the bacterial strain for use in the invention has a chromosome with sequence identity to SEQ ID NO:3, for example as described above, and a 16S rRNA sequence with sequence identity to any of SEQ ID NO:1 or 2, for example as described above, preferably with a 16s rRNA sequence that is at least 99% identical to SEQ ID NO:2, more preferably which comprises the 16S rRNA sequence of SEQ ID NO:2, and optionally comprises a plasmid with sequence identity to SEQ ID NO:4, as described above.

In certain embodiments, the bacterial strain for use in the invention has a chromosome with sequence identity to SEQ ID NO:3, for example as described above, and optionally comprises a plasmid with sequence identity to SEQ ID NO:4, as described above, and is effective for treating or preventing cancer.

In certain embodiments, the bacterial strain for use in the invention has a chromosome with sequence identity to SEQ ID NO:3, for example as described above, and a 16S rRNA sequence with sequence identity to any of SEQ ID NOs: 1 or 2, for example as described above, and optionally comprises a plasmid with sequence identity to SEQ ID NO:4, as described above, and is effective for treating or preventing cancer.

In certain embodiments, the bacterial strain for use in the invention has a 16s rRNA sequence that is at least 99%, 99.5% or 99.9% identical to the 16s rRNA sequence represented by SEQ ID NO: 2 (for example, which comprises the 16S rRNA sequence of SEQ ID NO:2) and a chromosome with at least 95% sequence identity to SEQ ID NO:3 across at least 90% of SEQ ID NO:3, and optionally comprises a plasmid with sequence identity to SEQ ID NO:4, as described above, and which is effective for treating or preventing cancer.

In certain embodiments, the bacterial strain for use in the invention has a 16s rRNA sequence that is at least 99%, 99.5% or 99.9% identical to the 16s rRNA sequence represented by SEQ ID NO: 2 (for example, which comprises the 16S rRNA sequence of SEQ ID NO:2) and a chromosome with at least 98% sequence identity (e.g. at least 99% or at least 99.5% sequence identity) to SEQ ID NO:3 across at least 98% (e.g. across at least 99% or at least 99.5%) of SEQ ID NO:3, and optionally comprises a plasmid with sequence identity to SEQ ID NO:4, as described above, and which is effective for treating or preventing cancer.

In certain embodiments, the bacterial strain for use in the invention is a Enterococcus gallinarum and has a 16s rRNA sequence that is at least 99%, 99.5% or 99.9% identical to the 16s rRNA sequence represented by SEQ ID NO: 2 (for example, which comprises the 16S rRNA sequence of SEQ ID NO:2) and a chromosome with at least 98% sequence identity (e.g. at least 99% or at least 99.5% sequence identity) to SEQ ID NO:3 across at least 98% (e.g. across at least 99% or at least 99.5%) of SEQ ID NO:3, and optionally comprises a plasmid with sequence identity to SEQ ID NO:4, as described above, and which is effective for treating or preventing cancer.

Alternatively, strains that are biotypes of the bacterium deposited under accession number NCIMB 42488 and that are suitable for use in the invention may be identified by using the accession number NCIMB 42488 deposit and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing. In preferred embodiments, such techniques may be used to identify other Enterococcus gallinarum strains.

In certain embodiments, strains that are biotypes of the bacterium deposited under accession number NCIMB 42488 and that are suitable for use in the invention are strains that provide the same pattern as the bacterium deposited under accession number NCIMB 42488 when analyzed by amplified ribosomal DNA restriction analysis (ARDRA), for example when using Sau3AI restriction enzyme (for exemplary methods and guidance see, for example,[19]). Alternatively, biotype strains are identified as strains that have the same carbohydrate fermentation patterns as the bacterium deposited under accession number NCIMB 42488. In some embodiments, the carbohydrate fermentation pattern is determined using the API 50 CHL panel (bioMérieux). In some embodiments, the bacterial strain used in the invention is:

positive for fermentation of at least one of (e.g. at least 2, 3, 4, 5, 6, 7, 8, 9, 10, 11, 12, 13, 14, 15, 16, 17 or all of): L-arabinose, D-ribose, D-xylose, D-galactose, D-glucose, D-fructose, D-mannose, N-acetylglucosamine, amygdalin, arbutin, salicin, D-cellobiose, D-maltose, sucrose, D-trehalose, gentiobiose, D-tagatose and potassium gluconate; and/or intermediate for fermentation of at least one of (e.g. at least 2, 3, 4 or all of): D-mannitol, Methyl-αD-glycopyranoside, D-lactose, starch, and L-fucose; preferably as determined by API 50 CHL analysis (preferably using the API 50 CHL panel from bioMérieux).

Other Enterococcus gallinarum strains that are useful in the compositions and methods of the invention, such as biotypes of the bacterium deposited under accession number NCIMB 42488, may be identified using any appropriate method or strategy, including the assays described in the examples. For instance, strains for use in the invention may be identified by culturing in anaerobic YCFA and/or administering the bacteria to the type II collagen-induced arthritis mouse model and then assessing cytokine levels. In particular, bacterial strains that have similar growth patterns, metabolic type and/or surface antigens to the bacterium deposited under accession number NCIMB 42488 may be useful in the invention. A useful strain will have comparable immune modulatory activity to the NCIMB 42488 strain. In particular, a biotype strain will elicit comparable effects on the cancer disease models to the effects shown in the Examples, which may be identified by using the culturing and administration protocols described in the Examples.

In some embodiments, the bacterial strain used in the invention is:

Positive for at least one of (e.g. at least 2, 3, 4, 5, 6, 7 or all of): mannose fermentation, glutamic acid decarboxylase, arginine arylamidase, phenylalanine arylamidase, pyroglutamic acid arylamidase, tyrosine arylamidase, histidine arylamidase and serine arylamidase; and/or Intermediate for at least one of (e.g. at least 2 or all of): β-galactosidase-6-phosphate, β-glucosidase and N-acetyl-β-glucosaminidase; and/or Negative for at least one of (e.g. at least 2, 3, 4, 5, 6 or all of): Raffinose fermentation, Proline arylamidase, Leucyl glycine arylamidase, Leucine arylamidase, Alanine arylamidase, Glycine arylamidase and Glutamyl glutamic acid arylamidase, preferably as determined by an assay of carbohydrate, amino acid and nitrate metabolism, and optionally an assay of alkaline phosphatase activity, more preferably as determined by Rapid ID 32A analysis (preferably using the Rapid ID 32A system from bioMérieux).

In some embodiments, the bacterial strain used in the invention is:

Negative for at least one of (e.g. at least 2, 3, or all 4 of) glycine arylamidase, raffinose fermentation, proline arylamidase, and leucine arylamidase, for example, as determined by an assay of carbohydrate, amino acid and nitrate metabolism, preferably as determined by Rapid ID 32A analysis (preferably using the Rapid ID 32A system from bioMérieux); and/or Intermediate positive for fermentation of L-fucose, preferably as determined by API 50 CHL analysis (preferably using the API 50 CHL panel from bioMérieux).

In some embodiments, the bacterial strain used in the invention is an extracellular ATP producer, for example one which produces 6-6.7 ng/μl (for example, 6.1-6.6 ng/μl or 6.2-6.5 ng/μl or 6.33±0.10 ng/μl) of ATP as measured using the ATP Assay Kit (Sigma-Aldrich, MAK190). Bacterial extracellular ATP can have pleiotropic effects including activation of T cell-receptor mediated signalling (Schenk et al., 2011), promotion of intestinal Th17 cell differentiation (Atarashi et al., 2008) and induction of secretion of the pro-inflammatory mediator IL-1β by activating the NLRP3 inflammasome (Karmarkar et al., 2016). Accordingly, a bacterial strain which is an extracellular ATP producer is useful for treating or preventing cancer.

In some embodiments, the bacterial strain for use in the invention comprises one or more of the following three genes: Mobile element protein; Xylose ABC transporter, permease component; and FIG00632333: hypothetical protein. For example, in certain embodiments, the bacterial strain for use in the invention comprises genes encoding Mobile element protein and Xylose ABC transporter, permease component; Mobile element protein and FIG00632333: hypothetical protein; Xylose ABC transporter, permease component and FIG00632333: hypothetical protein; or Mobile element protein, Xylose ABC transporter, permease component, and FIG00632333: hypothetical protein.

A particularly preferred strain of the invention is the *Enterococcus gallinarum* strain deposited under accession number NCIMB 42488. This is the exemplary MRX518 strain tested in the examples and shown to be effective for treating disease. Therefore, the invention provides a cell, such as an isolated cell, of the *Enterococcus gallinarum* strain deposited under accession number NCIMB 42488, or a derivative thereof. The invention also provides a composition comprising a cell of the *Enterococcus gallinarum* strain deposited under accession number NCIMB 42488, or a derivative thereof. The invention also provides a biologically pure culture of the *Enterococcus gallinarum* strain deposited under accession number NCIMB 42488. The invention also provides a cell of the *Enterococcus gallinarum* strain deposited under accession number NCIMB 42488, or a derivative thereof, for use in therapy, in particular for the diseases described herein. A derivative of the strain deposited under accession number NCIMB 42488 may be a daughter strain (progeny) or a strain cultured (subcloned) from the original.

A derivative of a strain of the invention may be modified, for example at the genetic level, without ablating the biological activity. In particular, a derivative strain of the invention is therapeutically active. A derivative strain will have comparable immune modulatory activity to the original NCIMB 42488 strain. In particular, a derivative strain will elicit comparable effects on the cancer disease models to the effects shown in the Examples, which may be identified by using the culturing and administration protocols described in the Examples. A derivative of the NCIMB 42488 strain will generally be a biotype of the NCIMB 42488 strain.

References to cells of the *Enterococcus gallinarum* strain deposited under accession number NCIMB 42488 encompass any cells that have the same safety and therapeutic efficacy characteristics as the strains deposited under accession number NCIMB 42488, and such cells are encompassed by the invention. Thus, in some embodiments, reference to cells of the *Enterococcus gallinarum* strain deposited under accession number NCIMB 42488 refers only to the MRX518 strain deposited under NCIMB 42488 and does not refer to a bacterial strain that was not deposited under NCIMB 42488. In some embodiments, reference to cells of the *Enterococcus gallinarum* strain deposited under accession number NCIMB 42488 refers to cells that have the same safety and therapeutic efficacy characteristics as the strains deposited under accession number NCIMB 42488, but which are not the strain deposited under NCIMB 42488.

In preferred embodiments, the bacterial strains in the compositions of the invention are viable and capable of partially or totally colonizing the intestine.

Treating Cancer

In preferred embodiments, the compositions of the invention are for use in treating or preventing cancer. The examples demonstrate that administration of the compositions of the invention can lead to a reduction in tumor growth in a number of tumor models.

In certain embodiments, treatment with the compositions of the invention results in a reduction in tumor size or a reduction in tumor growth. In certain embodiments, the compositions of the invention are for use in reducing tumor size or reducing tumor growth. The compositions of the invention may be effective for reducing tumor size or growth. In certain embodiments, the compositions of the invention are for use in subjects with solid tumors. In certain embodiments, the compositions of the invention are for use in reducing or preventing angiogenesis in the treatment of cancer. The compositions of the invention may have an effect on the immune or inflammatory systems, which have central roles in angiogenesis. In certain embodiments, the compositions of the invention are for use in preventing metastasis.

In certain embodiments, the compositions of the invention are for use in treating or preventing breast cancer. The examples demonstrate that the compositions of the invention may be effective for treating breast cancer. In certain embodiments, the compositions of the invention are for use in reducing tumor size, reducing tumor growth, or reducing angiogenesis in the treatment of breast cancer. In preferred embodiments the cancer is mammary carcinoma. In preferred embodiments the cancer is stage IV breast cancer.

In certain embodiments, the compositions of the invention are for use in treating or preventing lung cancer. The examples demonstrate that the compositions of the invention may be effective for treating lung cancer. In certain embodiments, the compositions of the invention are for use in reducing tumor size, reducing tumor growth, or reducing angiogenesis in the treatment of lung cancer. In preferred embodiments the cancer is lung carcinoma.

In certain embodiments, the compositions of the invention are for use in treating or preventing liver cancer. The examples demonstrate that the compositions of the invention may be effective for treating liver cancer. In certain embodiments, the compositions of the invention are for use in reducing tumor size, reducing tumor growth, or reducing angiogenesis in the treatment of liver cancer. In preferred embodiments the cancer is hepatoma (hepatocellular carcinoma).

In certain embodiments, the compositions of the invention are for use in treating or preventing colon cancer. The examples demonstrate that the compositions of the invention have an effect on colon cancer cells and may be effective for treating colon cancer. In certain embodiments, the compositions of the invention are for use in reducing tumor size, reducing tumor growth, or reducing angiogenesis in the treatment of colon cancer. In preferred embodiments the cancer is colorectal adenocarcinoma.

In some embodiments, the cancer is of the intestine. In some embodiments, the cancer is of a part of the body which is not the intestine. In some embodiments, the cancer is not cancer of the intestine. In some embodiments, the cancer is not colorectal cancer. In some embodiments, the cancer is not cancer of the small intestine. In some embodiments, the treating or preventing occurs at a site other than at the intestine. In some embodiments, the treating or preventing occurs at the intestine and also at a site other than at the intestine.

In certain embodiments, the compositions of the invention are for use in treating or preventing carcinoma. The examples demonstrate that the compositions of the invention may be effective for treating numerous types of carcinoma. In certain embodiments, the compositions of the invention are for use in treating or preventing non-immunogenic cancer. The examples demonstrate that the compositions of the invention may be effective for treating non-immunogenic cancers.

The therapeutic effects of the compositions of the invention on cancer may be mediated by a pro-inflammatory mechanism. Examples 2, 4 and 5 demonstrate that the expression of a number of pro-inflammatory cytokines may be increased following administration of MRX518. Inflammation can have a cancer-suppressive effect [20] and pro-inflammatory cytokines such as TNFα are being investigated as cancer therapies [21]. The up-regulation of genes such as TNF shown in the examples may indicate that the compositions of the invention may be useful for treating cancer via a similar mechanism. The up-regulation of CXCR3 ligands (CXCL9, CXCL10) and IFNγ-inducible genes (IL-32) may indicate that the compositions of the invention elicit an IFNγ-type response. IFNγ is a potent macrophage-activating factor that can stimulate tumirocidal activity [22], and CXCL9 and CXCL10, for example, also have anti-cancer effects [23-25]. Therefore, in certain embodiments, the compositions of the invention are for use in promoting inflammation in the treatment of cancer. In preferred embodiments, the compositions of the invention are for use in promoting Th1 inflammation in the treatment of cancer. Th1 cells produce IFNγ and have potent anti-cancer effects [20]. In certain embodiments, the compositions of the invention are for use in treating an early-stage cancer, such as a cancer that has not metastasized, or a stage 0 or stage 1 cancer. Promoting inflammation may be more effective against early-stage cancers [20]. In certain embodiments, the compositions of the invention are for use in promoting inflammation to enhance the effect of a second anti-cancer agent. In certain embodiments, the treatment or prevention of cancer comprises increasing the level of expression of one or more cytokines. For example, in certain embodiments, the treatment or prevention of cancer comprises increasing the level of expression of one or more of IL-1β, IL-6 and TNF-α, for example, IL-1β and IL-6, IL-1β and TNF-α, IL-6 and TNF-α or all three of IL-1β, IL-6 and TNF-α. Increases in levels of expression of any of IL-1β, IL-6 and TNF-α are known to be indicative of efficacy in treatment of cancer.

Examples 4 and 5 demonstrate that when a bacterial strain as described herein is used in combination with lipopolysaccharide (LPS), there is a synergistic increase in IL-1β. LPS is known to elicit a pro-inflammatory effect. Thus, in certain embodiments, the treatment or prevention comprises using a bacterial strain as described herein in combination with an agent that upregulates IL-1β. In certain embodiments, the treatment or prevention comprises using a bacterial strain as described herein in combination with LPS. Accordingly, a composition of the invention may additionally comprise an agent that upregulates IL-1β. Accordingly, a composition of the invention may additionally comprise LPS.

In certain embodiments, the compositions of the invention are for use in treating a subject that has previously received chemotherapy. In certain embodiments, the compositions of the invention are for use in treating a subject that has not tolerated a chemotherapy treatment. The compositions of the invention may be particularly suitable for such subjects. In some instances, a subject is in need thereof.

In certain embodiments, the compositions of the invention are for preventing relapse. The compositions of the invention may be suitable for long-term administration. In certain embodiments, the compositions of the invention are for use in preventing progression of cancer.

In certain embodiments, the compositions of the invention are for use in treating non-small-cell lung carcinoma. In certain embodiments, the compositions of the invention are for use in treating small-cell lung carcinoma. In certain embodiments, the compositions of the invention are for use in treating squamous-cell carcinoma. In certain embodiments, the compositions of the invention are for use in treating adenocarcinoma. In certain embodiments, the compositions of the invention are for use in treating glandular tumors, carcinoid tumors, or undifferentiated carcinomas.

In certain embodiments, the compositions of the invention are for use in treating hepatoblastoma, cholangiocarcinoma, cholangiocellular cystadenocarcinoma or liver cancer resulting from a viral infection.

In certain embodiments, the compositions of the invention are for use in treating invasive ductal carcinoma, ductal carcinoma in situ or invasive lobular carcinoma.

In further embodiments, the compositions of the invention are for use in treating or preventing acute lymphoblastic leukemia (ALL), acute myeloid leukemia, adrenocortical carcinoma, basal-cell carcinoma, bile duct cancer, bladder cancer, bone tumor, osteosarcoma/malignant fibrous histiocytoma, brainstem glioma, brain tumor, cerebellar astrocytoma, cerebral astrocytoma/malignant glioma, ependymoma, medulloblastoma, supratentorial primitive neuroectodermal tumors, breast cancer, bronchial adenomas/carcinoids, Burkitt's lymphoma, carcinoid tumor, cervical cancer, chronic lymphocytic leukemia, chronic myelogenous leukemia, chronic myeloproliferative disorders, colon cancer, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumor, gastrointestinal stromal tumor (GIST), germ cell tumor, glioma, childhood visual pathway and hypothalamic, Hodgkin lymphoma, melanoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer.

The compositions of the invention may be particularly effective when used in combination with further therapeutic agents. The immune-modulatory effects of the compositions of the invention may be effective when combined with more direct anti-cancer agents. Therefore, in certain embodiments, the invention provides a composition comprising a bacterial strain of the species *Enterococcus gallinarum* and an anticancer agent. In preferred embodiments the anticancer agent is an immune checkpoint inhibitor, a targeted antibody immunotherapy, a CAR-T cell therapy, an oncolytic virus, or a cytostatic drug. In preferred embodiments, the composition comprises an anti-cancer agent selected from the group consisting of: Yervoy (ipilimumab, BMS); Keytruda (pembrolizumab, Merck); Opdivo (nivolumab, BMS); MEDI4736 (AZ/MedImmune); MPDL3280A (Roche/Genentech); Tremelimumab (AZ/MedImmune); CT-011 (pidilizumab, CureTech); BMS-986015 (lirilumab, BMS); MEDI0680 (AZ/MedImmune); MSB-0010718C (Merck); PF-05082566 (Pfizer); MEDI6469 (AZ/MedImmune); BMS-986016 (BMS); BMS-663513 (urelumab, BMS); IMP321 (Prima Biomed); LAG525 (Novartis); ARGX-110 (arGEN-X); PF-05082466 (Pfizer); CDX-1127 (varlilumab; CellDex Therapeutics); TRX-518 (GITR Inc.); MK-4166 (Merck); JTX-2011 (Jounce Therapeutics); ARGX-115 (arGEN-X); NLG-9189 (indoximod, NewLink Genetics); INCB024360 (Incyte); IPH2201 (Innate Immotherapeutics/AZ); NLG-919 (NewLink Genetics); anti-VISTA (JnJ); Epacadostat (INCB24360, Incyte); F001287 (Flexus/BMS); CP 870893 (University of Pennsylvania); MGA271 (Macrogenix); Emactuzumab (Roche/Genentech); Galunisertib (Eli Lilly); Ulocuplumab (BMS); BKT140/BL8040 (Biokine Therapeutics); Bavituximab (Peregrine Pharmaceuticals); CC 90002 (Celgene); 852A (Pfizer); VTX-2337 (VentiRx Pharmaceuticals); IMO-2055 (Hybridon, Idera Pharmaceuticals); LY2157299 (Eli Lilly); EW-7197 (Ewha Women's University, Korea); Vemurafenib (Plexxikon); Dabrafenib (Genentech/GSK); BMS-777607 (BMS); BLZ945 (Memorial Sloan-Kettering Cancer Centre); Unituxin (dinutuximab, United Therapeutics Corporation); Blincyto (blinatumomab, Amgen); Cyramza (ramucirumab, Eli Lilly); Gazyva (obinutuzumab, Roche/Biogen); Kadcyla (ado-trastuzumab emtansine, Roche/Genentech); Perjeta (pertuzumab, Roche/Genentech); Adcetris (brentuximab vedotin, Takeda/Millennium); Arzerra (ofatumumab, GSK); Vectibix (panitumumab, Amgen); Avastin (bevacizumab, Roche/Genentech); Erbitux (cetuximab, BMS/Merck); Bexxar (tositumomab-I131, GSK); Zevalin (ibritumomab tiuxetan, Biogen); Campath (alemtuzumab, Bayer); Mylotarg (gemtuzumab ozogamicin, Pfizer); Herceptin (trastuzumab, Roche/Genentech); Rittman (rituximab, Genentech/Biogen); volociximab (Abbvie); Enavatuzumab (Abbvie); ABT-414 (Abbvie); Elotuzumab (Abbvie/BMS); ALX-0141 (Ablynx); Ozaralizumab (Ablynx); Actimab-C (Actinium); Actimab-P (Actinium); Milatuzumab-dox (Actinium); Emab-SN-38 (Actinium); Naptumonmab estafenatox (Active Biotech); AFM13 (Affimed); AFM11 (Affimed); AGS-16C3F (Agensys); AGS-16M8F (Agensys); AGS-22ME (Agensys); AGS-15ME (Agensys); GS-67E (Agensys); ALXN6000 (samalizumab, Alexion); ALT-836 (Altor Bioscience); ALT-801 (Altor Bioscience); ALT-803 (Altor Bioscience); AMG780 (Amgen); AMG 228 (Amgen); AMG820 (Amgen); AMG172 (Amgen); AMG595 (Amgen); AMG110 (Amgen); AMG232 (adecatumumab, Amgen); AMG211 (Amgen/MedImmune); BAY20-10112 (Amgen/Bayer); Rilotumumab (Amgen); Denosumab (Amgen); AMP-514 (Amgen); MEDI575 (AZ/MedImmune); MEDI3617 (AZ/MedImmune); MEDI6383 (AZ/MedImmune); MEDI551 (AZ/MedImmune); Moxetumomab pasudotox (AZ/MedImmune); MEDI565 (AZ/MedImmune); MEDI0639 (AZ/MedImmune); MEDI0680 (AZ/MedImmune); MEDI562 (AZ/MedImmune); AV-380 (AVEO); AV203 (AVEO); AV299 (AVEO); BAY79-4620 (Bayer); Anetumab ravtansine (Bayer); vantictumab (Bayer); BAY94-9343 (Bayer); Sibrotuzumab (Boehringer Ingleheim); BI-836845 (Boehringer Ingleheim); B-701 (BioClin); BIIB015 (Biogen); Obinutuzumab (Biogen/Genentech); BI-505 (Bioinvent); BI-1206 (Bioinvent); TB-403 (Bioinvent); BT-062 (Biotest) BIL-010t (Biosceptre); MDX-1203 (BMS); MDX-1204 (BMS); Necitumumab (BMS); CAN-4 (Cantargia AB); CDX-011 (Celldex); CDX1401 (Celldex); CDX301 (Celldex); U3-1565 (Daiichi Sankyo); patritumab (Daiichi Sankyo); tigatuzumab (Daiichi Sankyo); nimotuzumab (Daiichi Sankyo); DS-8895 (Daiichi Sankyo); DS-8873 (Daiichi Sankyo); DS-5573 (Daiichi Sankyo); MORab-004 (Eisai); MORab-009 (Eisai); MORab-003 (Eisai); MORab-066 (Eisai); LY3012207 (Eli Lilly); LY2875358 (Eli Lilly); LY2812176 (Eli Lilly); LY3012217 (Eli Lilly); LY2495655 (Eli Lilly); LY3012212 (Eli Lilly); LY3012211 (Eli Lilly); LY3009806 (Eli Lilly); cixutumumab (Eli Lilly); Flanvotumab (Eli Lilly); IMC-TR1 (Eli Lilly); Ramucirumab (Eli Lilly); Tabalumab (Eli Lilly); Zanolimumab (Emergent Biosolution); FG-3019 (FibroGen); FPA008 (Five Prime Therapeutics); FP-1039 (Five Prime Therapeutics); FPA144 (Five Prime Therapeutics); catumaxomab (Fresenius Biotech); IMAB362 (Ganymed); IMAB027 (Ganymed); HuMax-CD74 (Genmab); HuMax-TFADC (Genmab); GS-5745 (Gilead); GS-6624 (Gilead); OMP-21M18 (demcizumab, GSK); mapatumumab (GSK); IMGN289 (ImmunoGen); IMGN901 (ImmunoGen); IMGN853 (ImmunoGen); IMGN529 (ImmunoGen); IMMU-130 (Immunomedics); milatuzumab-dox (Immunomedics); IMMU-115 (Immunomedics); IMMU-132 (Immunomedics); IMMU-106 (Immunomedics); IMMU-102 (Immunomedics); Epratuzumab (Immunomedics); Clivatuzumab (Immunomedics); IPH41 (Innate Immunotherapeutics); Daratumumab (Janssen/Genmab); CNTO-95 (Intetumumab, Janssen); CNTO-328 (siltuximab, Janssen); KB004 (KaloBios); mogamulizumab (Kyowa Hakko Kirrin); KW-2871 (ecromeximab, Life Science); Sonepcizumab (Lpath); Margetuximab (Macrogenics); Enoblituzumab (Macrogenics); MGD006 (Macrogenics); MGF007 (Macrogenics); MK-0646 (dalotuzumab, Merck); MK-3475 (Merck); Sym004 (Symphogen/Merck Serono); DI17E6 (Merck Serono); MOR208 (Morphosys); MOR202 (Morphosys); Xmab5574 (Morphosys); BPC-1C (ensituximab, Precision Biologics); TAS266 (Novartis); LFA102 (Novartis); BHQ880 (Novartis/Morphosys); QGE031 (Novartis); HCD122 (lucatumumab, Novartis); LJM716 (Novartis); AT355 (Novartis); OMP-21M18 (Demcizumab, OncoMed); OMP52M51 (Oncomed/GSK); OMP-59R5 (Oncomed/GSK); vantictumab (Oncomed/Bayer); CMC-544 (inotuzumab ozogamicin, Pfizer); PF-03446962 (Pfizer); PF-04856884 (Pfizer); PSMA-ADC (Progenics); REGN1400 (Regeneron); REGN910 (nesvacumab, Regeneron/Sanofi); REGN421 (enoticumab, Regeneron/Sanofi); RG7221, RG7356, RG7155, RG7444, RG7116, RG7458, RG7598, RG7599, RG7600, RG7636, RG7450, RG7593, RG7596, DCDS3410A, RG7414 (parsatuzumab), RG7160 (imgatuzumab), RG7159 (obintuzumab), RG7686, RG3638 (onartuzumab), RG7597 (Roche/Genentech); SAR307746 (Sanofi); SAR566658 (Sanofi); SAR650984 (Sanofi); SAR153192 (Sanofi); SAR3419 (Sanofi); SAR256212 (Sanofi), SGN-LIV1A (lintuzumab, Seattle Genetics); SGN-CD33A (Seattle Genetics); SGN-75 (vorsetuzumab mafodotin, Seattle Genetics); SGN-19A (Seattle Genetics) SGN-CD70A (Seattle Genetics); SEA-CD40 (Seattle Genetics); ibritumomab tiuxetan (Spectrum); MLN0264 (Takeda); ganitumab (Takeda/Amgen); CEP-37250 (Teva); TB-403 (Thrombogenic); VB4-845 (Viventia); Xmab2512 (Xencor);

Xmab5574 (Xencor); nimotuzumab (YM Biosciences); Carlumab (Janssen); NY-ESO TCR (Adaptimmune); MAGE-A-10 TCR (Adaptimmune); CTL019 (Novartis); JCAR015 (Juno Therapeutics); KTE-C19 CAR (Kite Pharma); UCART19 (Cellectis); BPX-401 (Bellicum Pharmaceuticals); BPX-601 (Bellicum Pharmaceuticals); ATTCK20 (Unum Therapeutics); CAR-NKG2D (Celyad); Onyx-015 (Onyx Pharmaceuticals); H101 (Shanghai Sunwaybio); DNX-2401 (DNAtrix); VCN-01 (VCN Biosciences); Colo-Ad1 (PsiOxus Therapeutics); ProstAtak (Advantagene); Oncos-102 (Oncos Therapeutics); CG0070 (Cold Genesys); Pexa-vac (JX-594, Jennerex Biotherapeutics); GL-ONC1 (Genelux); T-VEC (Amgen); G207 (Medigene); HF10 (Takara Bio); SEPREHVIR (HSV1716, Virttu Biologics); OrienX010 (OrienGene Biotechnology); Reolysin (Oncolytics Biotech); SVV-001 (Neotropix); Cacatak (CVA21, Viralytics); Alimta (Eli Lilly), cisplatin, oxaliplatin, irinotecan, folinic acid, methotrexate, cyclophosphamide, 5-fluorouracil, Zykadia (Novartis), Tafinlar (GSK), Xalkori (Pfizer), Iressa (AZ), Gilotrif (Boehringer Ingelheim), Tarceva (Astellas Pharma), Halaven (Eisai Pharma), Veliparib (Abbvie), AZD9291 (AZ), Alectinib (Chugai), LDK378 (Novartis), Genetespib (Synta Pharma), Tergenpumatucel-L (NewLink Genetics), GV1001 (Kael-GemVax), Tivantinib (ArQule); Cytoxan (BMS); Oncovin (Eli Lilly); Adriamycin (Pfizer); Gemzar (Eli Lilly); Xeloda (Roche); Ixempra (BMS); Abraxane (Celgene); Trelstar (Debiopharm); Taxotere (Sanofi); Nexavar (Bayer); IMMU-132 (Immunomedics); E7449 (Eisai); Thermodox (Celsion); Cometriq (Exellxis); Lonsurf (Taiho Pharmaceuticals); Camptosar (Pfizer); UFT (Taiho Pharmaceuticals); and TS-1 (Taiho Pharmaceuticals).

In some embodiments, the one or more bacterial strains having a 16s rRNA sequence that is at least 95% identical to SEQ ID NO:2, for example which is an *Enterococcus gallinarum*, is/are the only therapeutically active agent(s) in a composition of the invention. In some embodiments, the bacterial strain(s) in the composition is/are the only therapeutically active agent(s) in a composition of the invention.

Modes of Administration

Preferably, the compositions of the invention are to be administered to the gastrointestinal tract in order to enable delivery to and/or partial or total colonization of the intestine with the bacterial strain of the invention. Generally, the compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a theobroma oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily.

In certain embodiments of the invention, treatment according to the invention is accompanied by assessment of the subject's gut microbiota. Treatment may be repeated if delivery of and/or partial or total colonization with the strain of the invention is not achieved such that efficacy is not observed, or treatment may be ceased if delivery and/or partial or total colonization is successful and efficacy is observed.

In certain embodiments, the composition of the invention may be administered to a pregnant animal, for example a mammal such as a human in order to reduce the likelihood of cancer developing in her child in utero and/or after it is born.

The compositions of the invention may be administered to a subject that has been diagnosed with cancer, or that has been identified as being at risk of a cancer. The compositions may also be administered as a prophylactic measure to prevent the development of cancer in a healthy subject.

The compositions of the invention may be administered to a subject that has been identified as having an abnormal gut microbiota. For example, the subject may have reduced or absent colonization by *Enterococcus gallinarum*.

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilized bacteria. Lyophilization of bacteria is a well-established procedure and relevant guidance is available in, for example, references [26-28].

Alternatively, the composition of the invention may comprise a live, active bacterial culture.

In some embodiments, the bacterial strain in the composition of the invention has not been inactivated, for example, has not been heat-inactivated. In some embodiments, the bacterial strain in the composition of the invention has not been killed, for example, has not been heat-killed. In some embodiments, the bacterial strain in the composition of the invention has not been attenuated, for example, has not been heat-attenuated. For example, in some embodiments, the bacterial strain in the composition of the invention has not been killed, inactivated and/or attenuated. For example, in some embodiments, the bacterial strain in the composition of the invention is live. For example, in some embodiments, the bacterial strain in the composition of the invention is viable. For example, in some embodiments, the bacterial strain in the composition of the invention is capable of partially or totally colonizing the intestine. For example, in some embodiments, the bacterial strain in the composition of the invention is viable and capable of partially or totally colonizing the intestine.

In some embodiments, the composition comprises a mixture of live bacterial strains and bacterial strains that have been killed.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [29] and [30].

The composition may be administered orally and may be in the form of a tablet, capsule or powder. Encapsulated products are preferred because *Enterococcus gallinarum* are anaerobes. Other ingredients (such as vitamin C, for example), may be included as oxygen scavengers and prebiotic substrates to improve the delivery and/or partial or total colonization and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention. A therapeutically effective amount of a bacterial strain is sufficient to exert a beneficial effect upon a subject. A therapeutically effective amount of a bacterial strain may be sufficient to result in delivery to and/or partial or total colonization of the subject's intestine.

A suitable daily dose of the bacteria, for example for an adult human, may be from about $1\times10^3$ to about $1\times10^{11}$ colony forming units (CFU); for example, from about $1\times10^7$ to about $1\times10^{10}$ CFU; in another example from about $1\times10^6$ to about $1\times10^{10}$ CFU.

In certain embodiments, the composition contains the bacterial strain in an amount of from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g of said composition.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [31]. Acceptable carriers or diluents for therapeutic use are well known in the pharmaceutical art and are described, for example, in reference [32]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilizing agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated with a nutritious product such as a milk-food product or a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yogurt, curdled milk, curd, sour milk, sour whole milk, butter milk and other sour milk products. Another important group includes milk beverages, such as whey beverages, fermented milks, condensed milks, infant or baby milks; flavored milks, ice cream; milk-containing food such as sweets.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism. Thus, in some embodiments, the invention provides a composition comprising one or more strains from the species *Enterococcus gallinarum*, which does not contain bacteria from any other species or which comprises only de minimis or biologically irrelevant amounts of bacteria from another species for use in therapy. In some embodiments, the composition consists essentially of *Enterococcus gallinarum*.

In some embodiments, the compositions of the invention comprise more than one bacterial strain or species. For example, in some embodiments, the compositions of the invention comprise more than one strain from within the same species (e.g. more than 1, 2, 3, 4, 5, 6, 7, 8, 9, 10, 15, 20, 25, 30, 35, 40 or 45 strains), and, optionally, do not contain bacteria from any other species. In some embodiments, the compositions of the invention comprise less than 50 strains from within the same species (e.g. less than 45, 40, 35, 30, 25, 20, 15, 12, 10, 9, 8, 7, 6, 5, 4 or 3 strains), and, optionally, do not contain bacteria from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 strains from within the same species and, optionally, do not contain bacteria from any other species. In some embodiments, the compositions of the invention comprise more than one species from within the same genus (e.g. more than 1, 2, 3, 4, 5, 6, 7, 8, 9, 10, 12, 15, 17, 20, 23, 25, 30, 35 or 40 species), and, optionally, do not contain bacteria from any other genus. In some embodiments, the compositions of the invention comprise less than 50 species from within the same genus (e.g. less than 50, 45, 40, 35, 30, 25, 20, 15, 12, 10, 8, 7, 6, 5, 4 or 3 species), and, optionally, do not contain bacteria from any other genus. In some embodiments, the compositions of the invention comprise 1-50, 1-40, 1-30, 1-20, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 species from within the same genus and, optionally, do not contain bacteria from any other genus. The invention comprises any combination of the foregoing.

In some embodiments, the composition comprises a microbial consortium. For example, in some embodiments, the composition comprises the bacterial strain having a 16s rRNA sequence that is at least 95% identical to SEQ ID NO:2, for example, which is an *Enterococcus gallinarum*, as part of a microbial consortium. For example, in some embodiments, the bacterial strain is present in combination with one or more (e.g. at least 2, 3, 4, 5, 10, 15 or 20) other bacterial strains from other genera with which it can live symbiotically in vivo in the intestine. For example, in some embodiments, the composition comprises a bacterial strain having a 16s rRNA sequence that is at least 95% identical to SEQ ID NO:2, for example, which is an *Enterococcus gallinarum*, in combination with a bacterial strain from a different genus. In some embodiments, the microbial consortium comprises two or more bacterial strains obtained from a faeces sample of a single organism, e.g. a human. In some embodiments, the microbial consortium is not found together in nature. For example, in some embodiments, the microbial consortium comprises bacterial strains obtained from faeces samples of at least two different organisms. In some embodiments, the two different organisms are from the same species, e.g. two different humans, e.g. two different human infants. In some embodiments, the two different organisms are an infant human and an adult human. In some embodiments, the two different organisms are a human and a non-human mammal.

In some embodiments, the composition of the invention additionally comprises a bacterial strain that has the same safety and therapeutic efficacy characteristics as strain MRX518, but which is not MRX518 deposited as NCIMB 42488, or which is not an *Enterococcus gallinarum*.

In some embodiments in which the composition of the invention comprises more than one bacterial strain, species or genus, the individual bacterial strains, species or genera may be for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strains, species or genera are stored separately but are mixed together prior to use.

In some embodiments, the bacterial strain for use in the invention is obtained from human infant faeces. In some embodiments in which the composition of the invention comprises more than one bacterial strain, all of the bacterial strains are obtained from human infant faeces or if other bacterial strains are present they are present only in de minimis amounts. The bacteria may have been cultured subsequent to being obtained from the human infant faeces and being used in a composition of the invention.

The compositions for use in accordance with the invention may or may not require marketing approval.

In certain embodiments, the invention provides the above pharmaceutical composition, wherein said bacterial strain is lyophilized. In certain embodiments, the invention provides the above pharmaceutical composition, wherein said bacterial strain is spray dried. In certain embodiments, the invention provides the above pharmaceutical composition, wherein the bacterial strain is lyophilized or spray dried and wherein it is live. In certain embodiments, the invention provides the above pharmaceutical composition, wherein the bacterial strain is lyophilized or spray dried and wherein it is viable. In certain embodiments, the invention provides the above pharmaceutical composition, wherein the bacterial strain is lyophilized or spray dried and wherein it is capable of partially or totally colonizing the intestine. In certain embodiments, the invention provides the above pharmaceutical composition, wherein the bacterial strain is lyophilized or spray dried and wherein it is viable and capable of partially or totally colonizing the intestine.

In some cases, the lyophilized or spray dried bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain as used in the invention; and a pharmaceutically acceptable excipient, carrier or diluent; wherein the bacterial strain is in an amount sufficient to treat a disorder when administered to a subject in need thereof; and wherein the disorder is breast cancer. In preferred embodiments the cancer is mammary carcinoma. In preferred embodiments the cancer is stage IV breast cancer.

In certain embodiments, the invention provides a pharmaceutical composition comprising: a bacterial strain as used in the invention; and a pharmaceutically acceptable excipient, carrier or diluent; wherein the bacterial strain is in an amount sufficient to treat a disorder when administered to a subject in need thereof; and wherein the disorder is lung cancer. In preferred embodiments the cancer is lung carcinoma.

In certain embodiments, the invention provides a pharmaceutical composition comprising: a bacterial strain as used in the invention; and a pharmaceutically acceptable excipient, carrier or diluent; wherein the bacterial strain is in an amount sufficient to treat a disorder when administered to a subject in need thereof; and wherein the disorder is liver cancer. In preferred embodiments the cancer is hepatoma (hepatocellular carcinoma).

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is colon cancer. In preferred embodiments the cancer is colorectal adenocarcinoma.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is carcinoma.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is a non-immunogenic cancer.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is selected from the group consisting of non-small-cell lung carcinoma, small-cell lung carcinoma, squamous-cell carcinoma, adenocarcinoma, glandular tumors, carcinoid tumors undifferentiated carcinomas.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is selected from the group consisting of hepatoblastoma, cholangiocarcinoma, cholangiocellular cystadenocarcinoma or liver cancer resulting from a viral infection.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is selected from the group consisting of invasive ductal carcinoma, ductal carcinoma in situ or invasive lobular carcinoma.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is selected from the group consisting of acute lymphoblastic leukemia (ALL), acute myeloid leukemia, adrenocortical carcinoma, basal-cell carcinoma, bile duct cancer, bladder cancer, bone tumor, osteosarcoma/malignant fibrous histiocytoma, brainstem glioma, brain tumor, cerebellar astrocytoma, cerebral astrocytoma/malignant glioma, ependymoma, medulloblastoma, supratentorial primitive neuroectodermal tumors, breast cancer, bronchial adenomas/carcinoids, Burkitt's lymphoma, carcinoid tumor, cervical cancer, chronic lymphocytic leukemia, chronic myelogenous leukemia, chronic myeloproliferative disorders, colon cancer, cutaneous T-cell lymphoma, endometrial cancer, ependymoma, esophageal cancer, Ewing's sarcoma, intraocular melanoma, retinoblastoma, gallbladder cancer, gastric cancer, gastrointestinal carcinoid tumor, gastrointestinal stromal tumor (GIST), germ cell tumor, glioma, childhood visual pathway and hypothalamic, Hodgkin lymphoma, melanoma, islet cell carcinoma, Kaposi sarcoma, renal cell cancer, laryngeal cancer, leukaemias, lymphomas, mesothelioma, neuroblastoma, non-Hodgkin lymphoma, oropharyngeal cancer, osteosarcoma, ovarian cancer, pancreatic cancer, parathyroid cancer, pharyngeal cancer, pituitary adenoma, plasma cell neoplasia, prostate cancer, renal cell carcinoma, retinoblastoma, sarcoma, testicular cancer, thyroid cancer, or uterine cancer.

In certain embodiments, the invention provides the above pharmaceutical composition, wherein the amount of the bacterial strain is from about $1\times10^3$ to about $1\times10^{11}$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation. For example, the composition may be provided as a tablet or capsule. In some embodiments, the capsule is a gelatine capsule ("gel-cap").

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [33]). In some embodiments, the formulation is an intrinsically enteric capsule (for example, Vcaps® from Capsugel).

In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

Culturing Methods

The bacterial strains for use in the present invention can be cultured using standard microbiology techniques as detailed in, for example, references [34-36].

The solid or liquid medium used for culture may be YCFA agar or YCFA medium. YCFA medium may include (per 100 ml, approximate values): Casitone (1.0 g), yeast extract (0.25 g), NaHCO$_3$ (0.4 g), cysteine (0.1 g), K$_2$HPO$_4$ (0.045 g), KH$_2$PO$_4$ (0.045 g), NaCl (0.09 g), (NH$_4$)$_2$SO$_4$ (0.09 g), MgSO$_4$.7H$_2$O (0.009 g), CaCl$_2$ (0.009 g), resazurin (0.1 mg), hemin (1 mg), biotin (1 µg), cobalamin (1 µg), p-aminobenzoic acid (3 µg), folic acid (5 µg), and pyridoxamine (15 µg).

Bacterial Strains for Use in Vaccine Compositions

The inventors have identified that the bacterial strains of the invention are useful for treating or preventing cancer. This is likely to be a result of the effect that the bacterial strains of the invention have on the host immune system. Therefore, the compositions of the invention may also be useful for preventing cancer, when administered as vaccine compositions. In certain such embodiments, the bacterial strains of the invention are viable. In certain such embodiments, the bacterial strains of the invention are capable of partially or totally colonizing the intestine. In certain such embodiments, the bacterial strains of the invention are viable and capable of partially or totally colonizing the intestine. In other certain such embodiments, the bacterial strains of the invention may be killed, inactivated or attenuated. In certain such embodiments, the compositions may comprise a vaccine adjuvant. In certain embodiments, the compositions are for administration via injection, such as via subcutaneous injection.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [37] and [38-44], etc.

A subject treated by a method described herein, or by contact with or administration of a composition described herein can be a mammalian subject who can be a human subject, a non-human primate, a canine mammal, a felid mammal or any other mammal. A subject maybe a patient who is a mammalian patient for instance, a human patient, a non-human primate, a canine mammal, a felid mammal or any other mammalian patient.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref [45]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref [46].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—Efficacy of Bacterial Inocula in Mouse Models of Cancer

Summary

This study tested the efficacy of compositions comprising an exemplary bacterial strain according to the invention in four tumor models.

Materials

Test Substance—

Bacterial strain #MRX518.

Reference Substance—

Anti-CTLA-4 antibody (clone: 9H10, catalog: BE0131, isotype: Syrian Hamster IgG1, Bioxcell).

Test and Reference Substances Vehicles—

Bacterial culture medium (Yeast extract, Casitone, Fatty Acid medium (YCFA)). Each day of injection to mice, antibody was diluted with PBS (ref: BE14-516F, Lonza, France).

Treatment Doses—

Bacteria: $2 \times 10^8$ in 200 µL. The a-CTLA-4 was injected at 10 mg/kg/inj. Anti-CTLA-4 was administered at a dose volume of 10 mL/kg/adm (i.e. for one mouse weighing 20 g, 200 µL of test substance will be administered) according to the most recent body weight of mice.

Routes of Administration—

Bacterial inoculum was administered by oral gavage (per os, PO) via a cannula. Cannulas were decontaminated every day. Anti-CTLA-4 was injected into the peritoneal cavity of mice (Intraperitoneally, IP).

Culture Conditions of Bacterial Strain—

The culture conditions for the bacterial strain were as follows:

Pipette 10 mL of YCFA (from the prepared 10 mL E&O lab bottles) into Hungate tubes Seal the tubes and flush with $CO_2$ using a syringe input and exhaust system Autoclave the Hungate tubes When cooled, inoculate the Hungate tubes with 1 mL of the glycerol stocks Place the tubes in a static 37° C. incubator for about 16 hours.

The following day, take 1 mL of this subculture and inoculate 10 mL of YCFA (pre-warmed flushed Hungate tubes again, all in duplicate)

Place them in a static 37° C. incubator for 5 to 6 h

Cancer Cell Line and Culture Conditions—

The cell lines that were used are detailed in the table below:

| Cell line | Type | Mouse strain | Origin |
|---|---|---|---|
| EMT-6 | Breast carcinoma | BALB/c | ATCC |
| LL/2 (LLC1) | Lung carcinoma | C57BL/6 | ATCC CRL1642 |
| Hepal-6 | Hepatocellular carcinoma | C57BL/6 | IPSEN INNOVATION |

The EMT-6 cell line was established from a transplantable murine mammary carcinoma that arose in a BALB/cCRGL mouse after implantation of a hyperplastic mammary alveolar nodule [47].

The LL/2 (LLC1) cell line was established from the lung of a C57BL mouse bearing a tumor resulting from an implantation of primary Lewis lung carcinoma [48].

The Hepa 1-6 cell line is a derivative of the BW7756 mouse hepatoma that arose in a C57/L mouse [49].

Cell Culture Conditions—

All cell lines were grown as monolayer at 37° C. in a humidified atmosphere (5% $CO_2$, 95% air). The culture medium and supplement are indicated in the table below:

| Cell line | Culture medium | Supplement |
|---|---|---|
| EMT6 | RPMI 1640 containing 2 mM L-glutamine (ref: BE12-702F, Lonza) | 10% fetal bovine serum (ref: #3302, Lonza) |
| LL/2 (LLC1) | RPMI 1640 containing 2 mM L-glutamine (ref: BE12-702F, Lonza) | 10% fetal bovine serum (ref: #3302, Lonza) |
| Hepal-6 | DMEM (ref: 11960-044, Gibco) | 10% fetal bovine serum (ref: #3302, Lonza) 2 mM L-Glutamine penicillin-streptomycin (Sigma G-6784) |

For experimental use, adherent tumor cells were detached from the culture flask by a 5 minute treatment with trypsin-versene (ref: BE17-161E, Lonza), in Hanks' medium without calcium or magnesium (ref: BE10-543F, Lonza) and neutralized by addition of complete culture medium. The cells were counted in a hemocytometer and their viability will be assessed by 0.25% trypan blue exclusion assay.

Use of Animals—

Healthy female Balb/C (BALB/cByJ) mice, of matching weight and age, were obtained from CHARLES RIVER (L'Arbresles) for the EMT6 model experiments.

Healthy female C57BL/6 (C57BL16J) mice, of matching weight and age, were obtained from CHARLES RIVER (L'Arbresles) for the LL/2 (LLC1) and the Hepa1-6 model experiments.

Animals were maintained in SPF health status according to the FELASA guidelines, and animal housing and experimental procedures according to the French and European Regulations and NRC Guide for the Care and Use of Laboratory Animals were followed [50,51]. Animals were maintained in housing rooms under controlled environmental conditions: Temperature: 22±2° C., Humidity 55±10%, Photoperiod (12 h light/12 h dark), HEPA filtered air, 15 air exchanges per hour with no recirculation. Animal enclosures were provided with sterile and adequate space with bedding material, food and water, environmental and social enrichment (group housing) as described: 900 cm² cages (ref: green, Tecniplast) in ventilated racks, Epicea bedding (SAFE), 10 kGy Irradiated diet (A04-10, SAFE), Complete food for immuno-competent rodents—R/M-H Extrudate, water from water bottles.

Experimental Design and Treatments

Antitumor Activity, EMT6 Model

Treatment Schedule—

The start of first dosing was considered as D0. On D0, non-engrafted mice were randomized according to their individual body weight into groups of 9/8 using Vivo Manager® software (Biosystemes, Couternon, France). On D0, the mice received vehicle (culture medium) or bacterial strain. On D14, all mice were engrafted with EMT-6 tumor cells as described below. On D24, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 8 | Untreated | — | — | — |
| 2 | 8 | Vehicle (media) | — | PO | Q1Dx42 |
| 3 | 9 | Bacterial strain #1 (MRX518) | 2 × 10⁸ bacteria | PO | Q1Dx42 |
| 4 | 8 | Anti-CTLA4 | 10 mg/kg | IP | TWx2 |

The monitoring of animals was performed as described below.

Induction of EMT6 Tumors in Animals—

On D14, tumors were induced by subcutaneous injection of 1×10⁶ EMT-6 cells in 200 µL RPMI 1640 into the right flank of mice.

Euthanasia—

Each mouse was euthanized when it reached a humane endpoint as described below, or after a maximum of 6 weeks post start of dosing.

Antitumor Activity, LL/2 (LLC1) Model

Treatment Schedule—

The start of first dosing was considered as D0. On D0, non-engrafted mice were randomized according to their individual body weight into 7 groups of 9/8 using Vivo Manager® software (Biosystemes, Couternon, France). On D0, the mice will received vehicle (culture medium) or bacterial strain. On D14, all mice were engrafted with LL/2 tumor cells as described below. On D27, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 8 | Untreated | — | — | — |
| 2 | 9 | Vehicle (media) | — | PO | Q1Dx42 |
| 3 | 9 | Bacterial strain #1 (MRX518) | 2 × 10⁸ bacteria | PO | Q1Dx42 |
| 4 | 8 | Anti-CTLA4 | 10 mg/kg | IP | TWx2 |

The monitoring of animals was performed as described below.

Induction of LL/2 (LLC1) Tumors in Animals—

On D14, tumors were induced by subcutaneous injection of 1×10⁶ LL/2 (LLC1) cells in 200 µL RPMI 1640 into the right flank of mice.

Euthanasia—

Each mouse was euthanized when it reached a humane endpoint as described below, or after a maximum of 6 weeks post start of dosing.

Antitumor Activity, Hepa1-6 Model

Treatment Schedule—

The start of first dosing was considered as D0. On D0, non-engrafted mice were randomized according to their individual body weight into 7 groups of 9 using Vivo Manager® software (Biosystemes, Couternon, France). On D0, the mice received vehicle (culture medium) or bacterial strain. On D14, all mice were engrafted with Hepa 1-6 tumor cells as described below. On D16, mice from the positive control group received anti-CTLA-4 antibody treatments.

The treatment schedule is summarized in the table below:

| Group | No. Animals | Treatment | Dose | Route | Treatment Schedule |
|---|---|---|---|---|---|
| 1 | 9 | Untreated | — | — | — |
| 2 | 9 | Vehicle (media) | — | PO | Q1Dx42 |
| 6 | 9 | Bacterial strain #4 (MRX518) | 2 × 10⁸ bacteria | PO | Q1Dx42 |
| 7 | 9 | Anti-CTLA4 | 10 mg/kg | IP | TWx2 |

The monitoring of animals was performed as described below.

Orthotopic Induction of Hepa 1-6 Tumor Cells in Animals by Intrasplenic Injection—

On D14, one million (1×10⁶) Hepa 1-6 tumor cells in 50 µL RPMI 1640 medium were transplanted via intra-splenic injection into mice. Briefly, a small left subcostal flank incision was made and the spleen was exteriorized. The spleen was exposed on a sterile gauze pad, and injected under visual control with the cell suspension with a 27-gauge needle. After the cell inoculation, the spleen was excised.

Euthanasia—

Each mouse was euthanized when it reached a humane endpoint as described in section below, or after a maximum of 6 weeks post start of dosing.

Evaluation of Tumor Burden at Euthanasia—

At the time of termination, livers were collected and weighed.

Animal Monitoring

Clinical Monitoring—

The length and width of the tumor was measured twice a week with callipers and the volume of the tumor was estimated by this formula [52]:

$$\text{Tumor volume} = \frac{\text{width}^2 \times \text{length}}{2}$$

Humane endpoints [53]: Signs of pain, suffering or distress: pain posture, pain face mask, behaviour; Tumor exceeding 10% of normal body weight, but non-exceeding 2000 mm³; Tumors interfering with ambulation or nutrition; Ulcerated tumor or tissue erosion; 20% body weight loss remaining for 3 consecutive days; Poor body condition, emaciation, cachexia, dehydration; Prolonged absence of voluntary responses to external stimuli; Rapid laboured breathing, anaemia, significant bleeding; Neurologic signs: circling, convulsion, paralysis; Sustained decrease in body temperature; Abdominal distension.

Anaesthesia—

Isoflurane gas anesthesia were used for all procedures: surgery or tumor inoculation, i.v. injections, blood collection. Ketamine and Xylazine anesthesia were used for stereotaxia surgical procedure.

Analgesia—

Carprofen or multimodal carprofen/buprenorphine analgesia protocol were adapted to the severity of surgical procedure. Non-pharmacological care was provided for all painful procedures. Additionally, pharmacological care not interfering with studies (topic treatment) were provided at the recommendation of the attending veterinarian.

Euthanasia—

Euthanasia of animals was performed by gas anesthesia over-dosage (Isoflurane) followed by cervical dislocation or exsanguination.

Results
Antitumor Activity, EMT6 Model

The results are shown in FIG. 1. Treatment with an exemplary bacterial strain of the invention led to a clear reduction in tumor volume relative to both the negative controls. The positive control also led to a reduction in tumor volume, as would be expected.

Antitumor Activity, LL/2 (LLC1) Model

Figure 2:
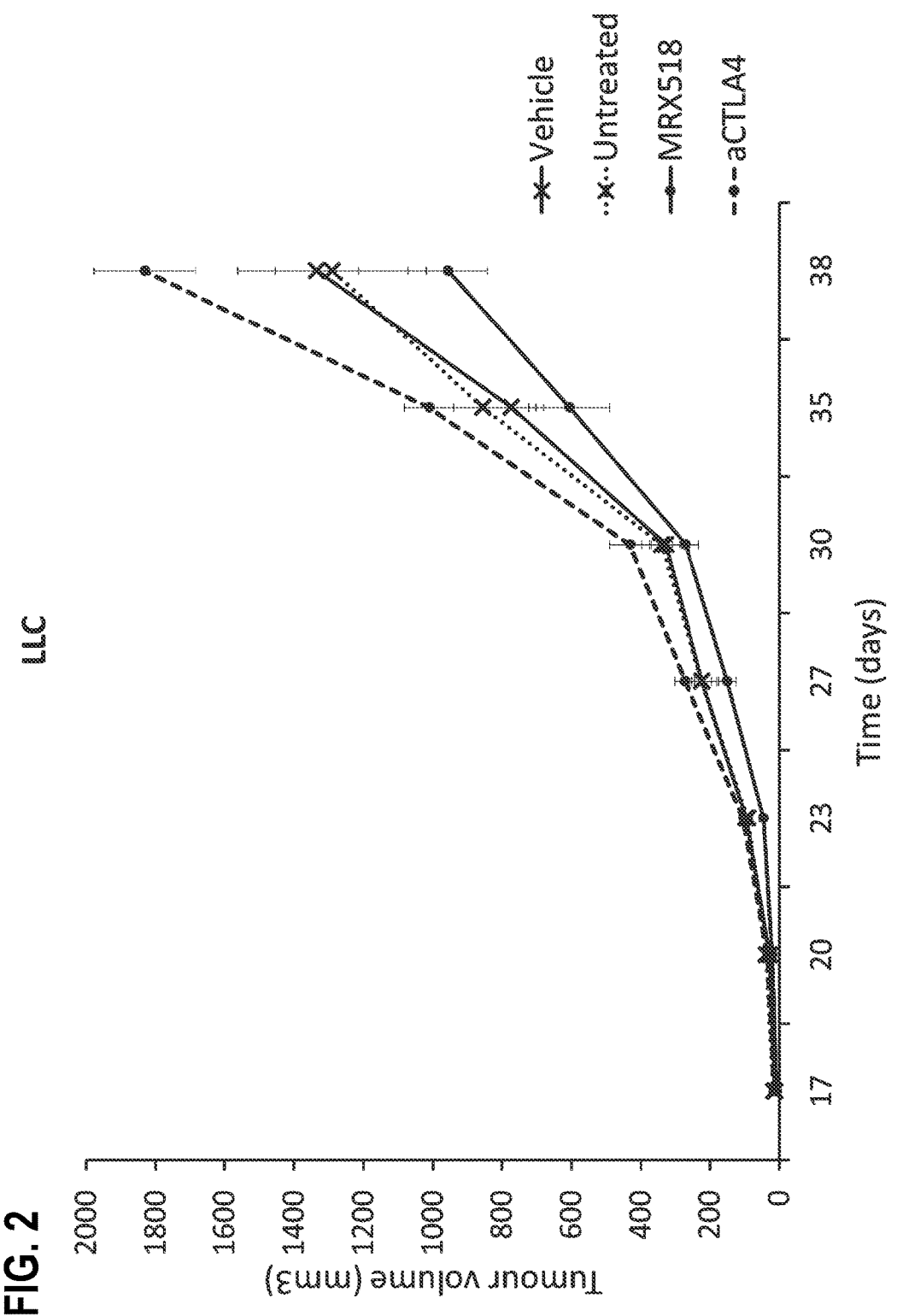
FIG. 2: Mouse model of lung cancer—tumor volume.

The results are shown in FIG. 2. Treatment with an exemplary bacterial strain of the invention led to a clear reduction in tumor volume relative to both the negative controls.

Antitumor Activity, Hepa1-6 Model

Figure 3:
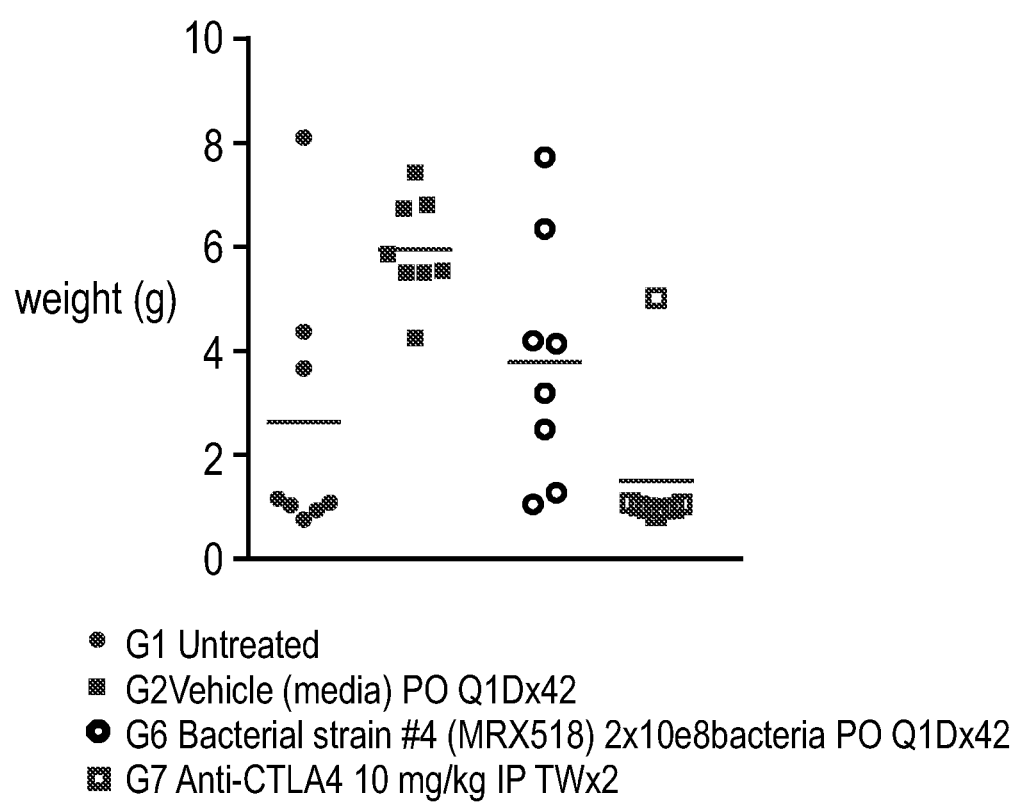
FIG. 3: Mouse model of liver cancer—liver weight.

The results are shown in FIG. 3. The untreated negative control does not appear as would be expected, because liver weight was lower in this group than the other groups. However, the vehicle negative control and the positive control groups both appear as would be expected, because mice treated with vehicle alone had larger livers than mice treated with anti-CTLA4 antibodies, reflecting a greater tumor burden in the vehicle negative control group. Treatment with an exemplary bacterial strain of the invention led to a clear reduction in liver weight (and therefore tumor burden) relative to the mice in the vehicle negative control group.

These data indicate that strain MRX518 may be useful for treating or preventing cancer, and in particular for reducing tumor volume in breast, lung and liver cancers.

Example 2—PCR Gene Analysis

A pure culture of bacteria MRX518 was studied in a PCR gene analysis. There were two arms to the experiment: 1) MRX518 was co-cultured with human colonic cells (CaCo2) to investigate the effects of the bacteria on the host, and 2) MRX518 was co-cultured on CaCo2 cells that were stimulated with IL1 to mimic the effect of the bacteria in an inflammatory environment. The effects in both scenarios were evaluated through gene expression analysis. The results are shown below:

| Gene | Fold change | Function |
| --- | --- | --- |
| CXCL3 | 28412.73 | CXCR2 ligand, |
| CXCL2 | 135.42 | CXCR2 ligand, 90% homology with CXCL1. |
| CXCL9 | 34.76 | CXCR3 ligand, primarily thought of as Th1 cell chemoattractant (inducible by IFN-g) |
| IL8 | 31.81 | Cytokine, chemoattractant (especially neutrophils), many receptors including CXCR1 and CXCR2/ |
| CXCL1 | 16.48 | CXCR2 ligand, stimulates cell proliferation as well as migration, overexpression is neuroprotective in EAE. |
| CD40 | 14.33 | Co-stimulatory molecule, route of T cell dependent DC activation. |
| TNF | 13.50 | Major proinflammatory cytokine |
| IL17C | 12.18 | Promotes antibacterial response from epthielium, synergistic with IL-22, |
| CXCL10 | 10.66 | Close homology with CXCL9, think also CXCR3 ligand |
| HSPA1B | 10.19 | Heat shock protein |
| NFKBIA | 8.87 | NFkB signalling; PI3K |
| JUN | 7.61 | Antibacterial response; GPCR signalling. |
| TNFAIP3 | 6.63 | TNF signalling |
| DUSP1 | 6.36 | Anti-inflammatory phosphatase, inactivates MAPKs |
| JUNB | 5.36 | Transcription factor, JAK-STAT signalling |
| BIRC3 | 4.86 | Adherens junctions, tight junctions |
| DUSP2 | 4.59 | Anti-inflammatory, inactivates MAPK. |
| IL32 | 4.29 | Proinflammatory cytokine, induced by IFN-g, IL-18 |
| DUSP5 | 3.12 | Anti-inflammatory, inactivates MAPK |
| FOS | 3.03 | Transcription factors, TLR signalling, forms part of AP-1 |
| GADD45B | 2.89 | Cell growth and proliferation |
| CLDN4 | 2.61 | Tight junctions |
| ADM | 2.57 | NFkB signalling |
| KLF10 | 2.49 | Cell arrest, TGF-b singllaing. |
| DEFB4A | −2.34 | Antimicrobial peptide |
| APBA1 | −2.53 | Signalling |
| IGFBP1 | −2.72 | Signalling pathway |
| IL28B | −2.73 | IFN-lambda, antiviral immune defence, |
| IL10 | −3.38 | Anti-inflammatory cytokine |
| NR4A1 | −5.57 | Nuclear receptor, anti-inflammatory, regulator of T cell proliferation. T helper cell differentiation |
| NOD2 | −14.98 | PRR, inflammasome activator, promotes autophagy |
| INOS | −26.88 | Proinflammatory, generator of nitric oxide |

These Data Appear to Show Two Gene Expression Signatures—

CXCR1/2 ligands (CXCL3, CXCL2, CXCL1, IL-8), which is associated with pro-inflammatory cell migration, and CXCR3 ligands (CXCL9,CXCL10), which is more specifically indicative of IFN-γ-type responses, also supported by IL-32, which is IFN-γ-inducible.

Example 3—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Example 4—Cytokine Production in Immature Dendritic Cells Induced by MRX518 Compared to MRX518+LPS Summary This study tested the effect of the bacterial strain MRX518 alone and in combination with lipopolysaccharide (LPS) on cytokine production in immature dendritic cells.

A monocyte population was isolated from peripheral blood mononuclear cells (PBMCs). The monocyte cells were subsequently differentiated into immature dendritic cells. The immature dendritic cells were plated out at 200,000 cells/well and incubated with MRX518 at a final concentration of $10^7$/ml, with the optional addition of LPS at a final concentration of 100 ng/ml. The negative control involved incubating the cells with RPMI media alone and positive controls incubated the cells with LPS at a final concentration of 100 ng/ml. The cytokine content of the cells was then analyzed.

Results

Figure 4A:
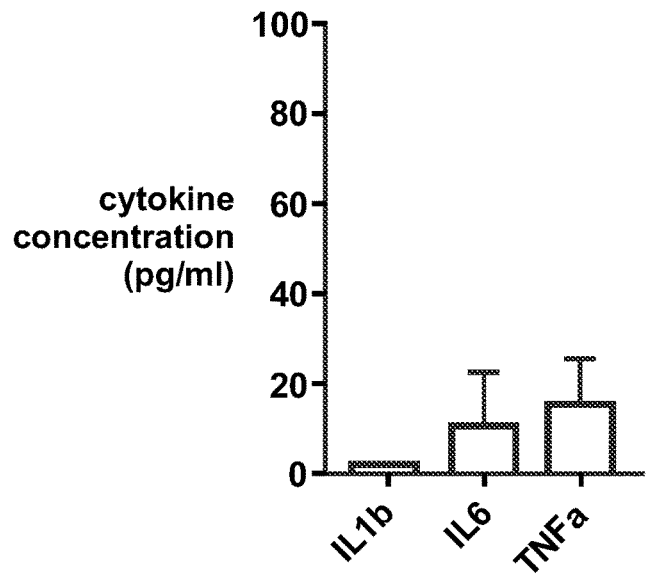
FIG. 4A: Cytokine levels (pg/ml) in immature dendritic cells (No bacteria).
Figure 4B:
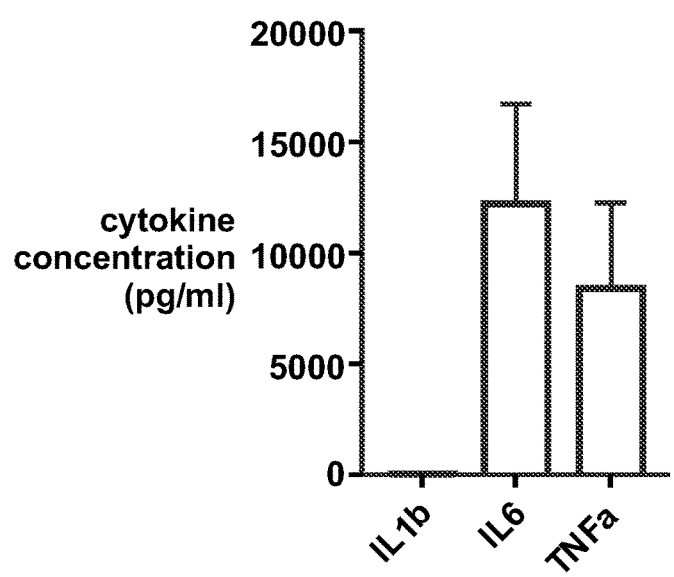
FIG. 4B: Cytokine levels (pg/ml) in immature dendritic cells after the addition of LPS.
Figure 4C:
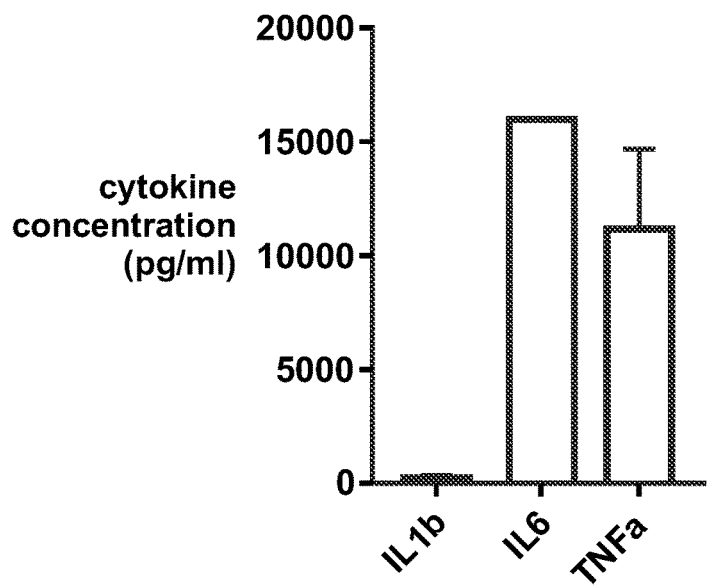
FIG. 4C: Cytokine levels (pg/ml) in immature dendritic cells after the addition of MRX518.
Figure 4D:
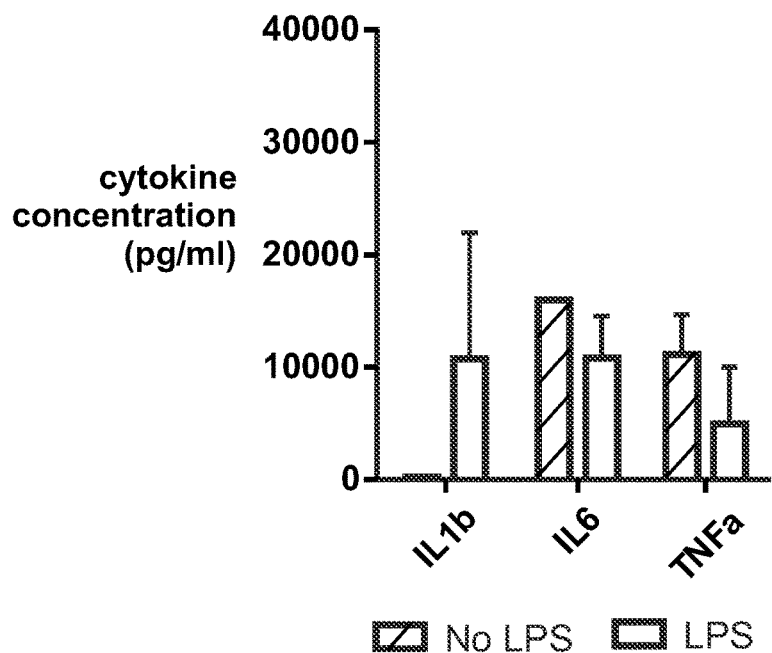
FIG. 4D: Cytokine levels (pg/ml) in immature dendritic cells after the addition of MRX518 and LPS.

The results of these experiments can be seen in FIGS. 4a-d. The addition of MRX518 alone leads to a substantial increase in the level of cytokines IL-6 and TNF-α compared to the negative control (FIGS. 4a and c). The addition of LPS (positive control) leads to an increase in the level of IL-6 and TNF-α compared to the negative control but not IL-1β (FIG. 4b). A combination of MRX518 and LPS led to a synergistic increase in the level of IL-1β produced (FIG. 4d).

Conclusion

MRX518 has the ability to induce higher IL-6 and TNF-α cytokine production in immature dendritic cells. The combination LPS and MRX518 can increase the levels of cytokines IL-1β in immature dendritic cells. These data indicate that MRX518 alone or in combination with LPS can increase inflammatory cytokines IL-1β, IL-6 and TNF-α, which promotes inflammation that can suppress cancer. Treatment with MRX518 alone or in combination with can induce cytokines that can limit tumor growth.

Example 5—Cytokine Production in THP-1 Cells Induced by MRX518 Compared to MRX518+LPS Summary This study tested the effect of bacterial strain MRX518 alone and in combination with LPS on cytokine production in THP-1 cells, a model cell line for monocytes and macrophages.

THF-1 cells were differentiated into M0 medium for 48 h with 5 ng/mL phorbol-12-myristate-13-acetate (PMA). These cells were subsequently incubated with MRX518 at a final concentration of $10^8$/ml, with or without the addition of LPS at a final concentration of 100 ng/ml. The bacteria were then washed off and the cells allowed to incubate under normal growing conditions for 24 h. The cells were then spun down and the resulting supernatant was analyzed for cytokine content.

Results

Figure 5A:
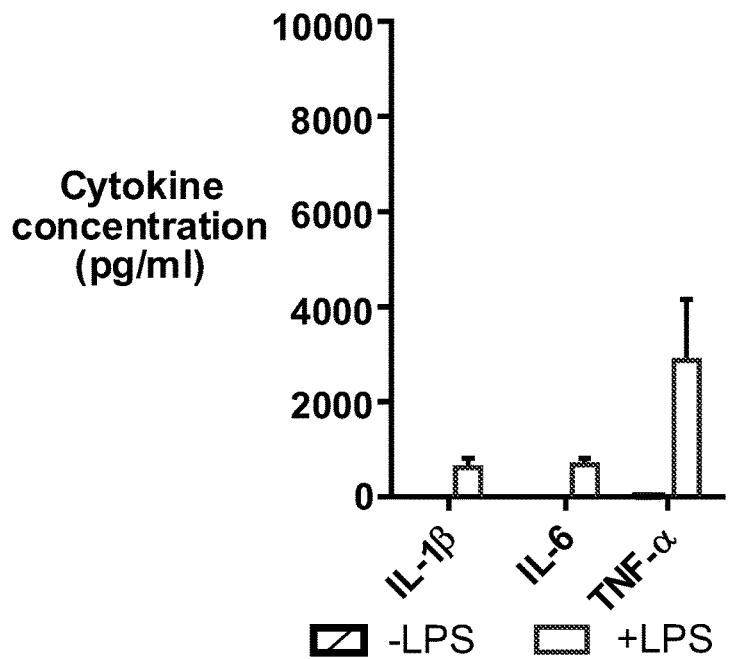
FIG. 5A: Cytokine levels in THP-1 cells (No bacteria).
Figure 5B:
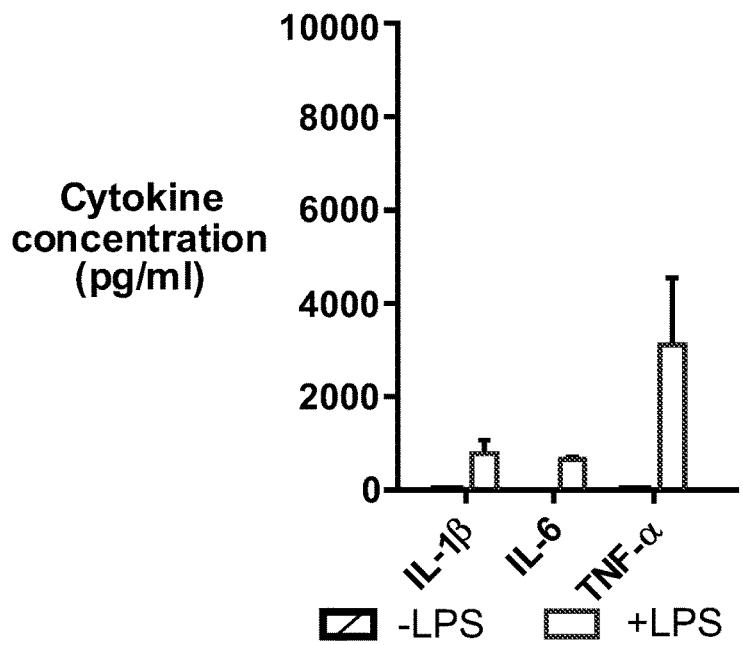
FIG. 5B: Cytokine levels in THP-1 cells after addition of bacterial sediment.
Figure 5C:
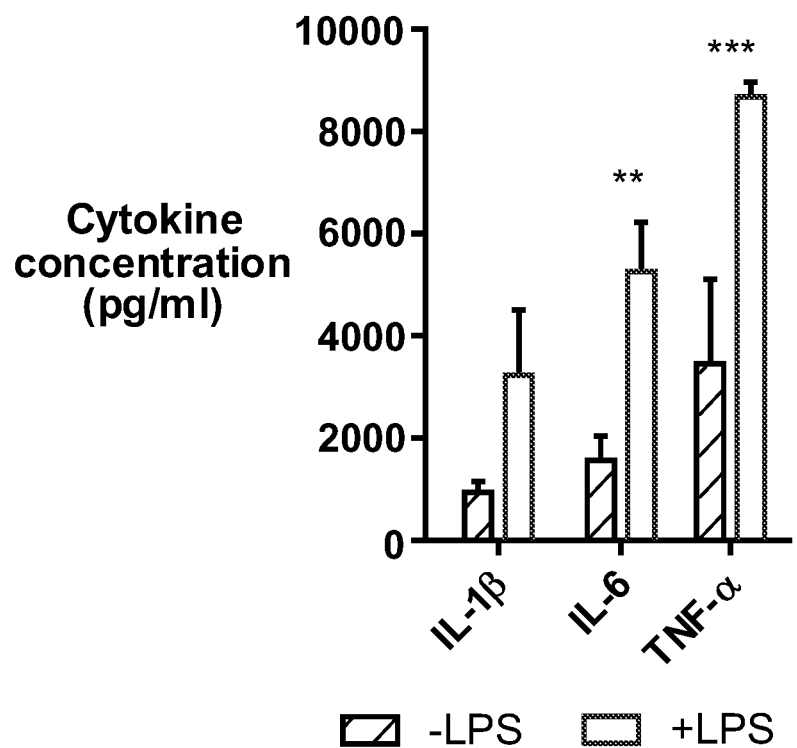
FIG. 5C: Cytokine levels in THP-1 cells after the addition of MRX518 alone or in combination with LPS.

The results of these experiments can be seen in FIGS. 5a-c. The addition of MRX518 without LPS leads to an increase in the cytokine levels of IL-1β, IL-6 and TNF-α compared to the no bacterial and the bacterial sediment controls. The addition of LPS and MRX518 leads to a synergistic increase in the production of cytokines.

Conclusion

MRX518 has the ability to induce cytokine production in THP-1 cells, which can be synergistically increased with the addition of LPS. These data indicate that MRX518 alone or in combination with LPS can increase inflammatory cytokines IL-1β, IL-6 and TNF-α, which promotes inflammation that can suppress cancer. Treatment with MRX518 alone or in combination with can induce cytokines that can limit tumor growth.

REFERENCES

[1] Spor et al. (2011) *Nat Rev Microbiol.* 9(4):279-90.
[2] Eckburg et al. (2005) *Science.* 10; 308(5728):1635-8.
[3] Macpherson et al. (2001) *Microbes Infect.* 3(12): 1021-35
[4] Macpherson et al. (2002) *Cell Mol Life Sci.* 59(12):2088-96.
[5] Mazmanian et al. (2005) *Cell* 15; 122(1):107-18.
[6] Frank et al. (2007) *PNAS* 104(34): 13780-5.
[7] Scanlan et al. (2006) *J Clin Microbiol.* 44(11):3980-8.
[8] Kang et al. (2010) *Inflamm Bowel Dis.* 16(12):2034-42.
[9] Machiels et al. (2013) *Gut.* 63(8):1275-83.
[10] WO 2013/050792
[11] WO 03/046580
[12] WO 2013/008039
[13] WO 2014/167338
[14] Goldin and Gorbach (2008) *Clin Infect Dis.* 46 Suppl 2:S96-100.
[15] Azad et al. (2013) *BMJ.* 347:f6471.
[16] Strickertsson et al. (2014) *Genes.* 5(3): 726-738.
[17] Collins et al. (1984) *Int J Syst Evol Microbiol.* 34: 220-223.
[18] Masco et al. (2003) *Systematic and Applied Microbiology,* 26:557-563.
[19] Srůková et al. (2011) *J. Microbiol. Methods,* 87(1): 10-6.
[20] Haabeth et al. (2012) *OncoImmunologyl* 1 (1):1146-1152.
[21] Lejeune et al. (2006) *Cancer Immun.* 6:6
[22] Pace et al. (1983) *PNAS.* 80:8782-6.
[23] Sgadari et al. (1996) *PNAS.* 93:13791-6.
[24] Arenberg et al. (1996) *J. Exp. Med.* 184:981-92.
[25] Sgadari et al. (1997) *Blood.* 89:2635-43.
[26] Miyamoto-Shinohara et al. (2008) *J. Gen. Appl. Microbiol.,* 54, 9-24.
[27] *Cryopreservation and Freeze-Drying Protocols,* ed. by Day and McLellan, Humana Press.
[28] Leslie et al. (1995) *Appl. Environ. Microbiol.* 61, 3592-3597.
[29] Mitropoulou et al. (2013) *J Nutr Metab.* (2013) 716861.
[30] Kailasapathy et al. (2002) *Curr Issues Intest Microbiol.* 3(2):39-48.
[31] *Handbook of Pharmaceutical Excipients,* 2nd Edition, (1994), Edited by A Wade and P J Weller
[32] *Remington's Pharmaceutical Sciences,* Mack Publishing Co. (A. R. Gennaro edit. 1985)
[33] US 2016/0067188
[34] *Handbook of Microbiological Media, Fourth Edition* (2010) Ronald Atlas, CRC Press.
[35] *Maintaining Cultures for Biotechnology and Industry* (1996) Jennie C. Hunter-Cevera, Academic Press
[36] Strobel (2009) *Methods Mol Biol.* 581:247-61.
[37] Gennaro (2000) *Remington: The Science and Practice of Pharmacy.* 20th edition, ISBN: 0683306472.
[38] *Molecular Biology Techniques: An Intensive Laboratory Course,* (Ream et al., eds., 1998, Academic Press).
[39] *Methods In Enzymology* (S. Colowick and N. Kaplan, eds., Academic Press, Inc.)
[40] *Handbook of Experimental Immunology,* Vols. I-IV (D. M. Weir and C. C. Blackwell, eds, 1986, Blackwell Scientific Publications)
[41] Sambrook et al. (2001) *Molecular Cloning: A Laboratory Manual,* 3rd edition (Cold Spring Harbor Laboratory Press).
[42] *Handbook of Surface and Colloidal Chemistry* (Birdi, K. S. ed., CRC Press, 1997)
[43] Ausubel et al. (eds) (2002) *Short protocols in molecular biology,* 5th edition (Current Protocols).
[44] *PCR (Introduction to Biotechniques Series),* 2nd ed. (Newton & Graham eds., 1997, Springer Verlag)
[45] *Current Protocols in Molecular Biology* (F. M. Ausubel et al., eds., 1987) Supplement 30
[46] Smith & Waterman (1981) *Adv. Appl. Math.* 2: 482-489.
[47] Rockwell et al., (1972) *J Natl Cancer Inst.* 49:735-49.
[48] Bertram and Janik (1980) *Cancer Lett.* 11:63-73.
[49] Darlington (1987) *Meth Enzymol.* 151:19-38.
[50] Principe d'éthique de l'expérimentation animale, Directive n° 2010/63 CEE 22 Sep. 2010, Décrêt n° 2013-118 1 Feb. 2013.
[51] Guide for the Care and Use of Laboratory Animals: Eighth Edition. The National Academies Press; 2011
[52] Simpson-Herren and Lloyd (1970) *Cancer Chemother Rep.* 54:143-74.
[53] Workman et al. (2010) *Br. J. Cancer.* 102:1555-77.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09974815B2). An electronic copy of the "Sequence Listing" will also be available from the USPTO upon request and payment of the fee set forth in 37 CFR 1.19(b)(3).

What is claimed is:

1. A method of treatment of cancer in a subject in need thereof, comprising: administering to the subject a therapeutically effective amount of a pharmaceutical composition that comprises: a bacteria strain with a 16s rRNA gene sequence with at least 99.5% sequence identity to the polynucleotide of SEQ ID NO:2, wherein the sequence identity is determined by the Smith-Waterman homology search algorithm using an affine gap search with a gap open penalty of 12 and a gap extension penalty of 2, and a BLOSUM matrix of 62; wherein said bacteria strain has a carbohydrate fermentation profile that comprises: (i) a positive fermentation of at least one of: L-arabinose and D-xylose; and (ii) an intermediate fermentation of Methyl-αD-glycopyranoside; wherein said bacteria strain is present in an amount sufficient for treatment of cancer in the subject, and wherein the cancer is a solid tumor cancer.

2. The method of claim 1, wherein said carbohydrate profile further comprises a positive fermentation of at least one of: D-tagatose, D-ribose, potassium gluconate, D-galactose, D-glucose, D-fructose, D-mannose, N-acetylglucosamine, amygdalin, arbutin, salicin, D-cellobiose, D-maltose, sucrose, D-trehalose, and gentiobiose.

3. The method of claim 1, wherein said carbohydrate profile further comprises an intermediate fermentation of at least one of: D-mannitol, D-lactose, and starch.

4. The method of claim 1, wherein said carbohydrate profile further comprises:
   (i) a positive fermentation of at least one of: D-tagatose, D-ribose, potassium gluconate, D-galactose, D-glucose, D-fructose, D-mannose, N-acetylglucosamine, amygdalin, arbutin, salicin, D-cellobiose, D-maltose, sucrose, D-trehalose, and gentiobiose; and
   (ii) an intermediate fermentation of at least one of: D-mannitol, D-lactose, and starch.

5. The method of claim 4, wherein said carbohydrate profile comprises a positive fermentation of L-arabinose, D-xylose, and gentiobiose.

6. The method of claim 4, wherein said carbohydrate profile comprises a positive fermentation of L-arabinose and D-xylose and an intermediate fermentation of Methyl-αD-glycopyranoside.

7. The method of claim 1, wherein the bacteria strain is live and viable.

8. The method of claim 1, wherein said bacteria strain comprises the 16s rRNA gene sequence of SEQ ID NO:2.

9. The method of claim 1, wherein said bacteria strain is of the species *Enterococcus gallinarum*.

10. The method of claim 1, wherein said bacteria strain is the bacteria strain deposited under accession number NCIMB 42488.

* * * * *

UNITED STATES PATENT AND TRADEMARK OFFICE
CERTIFICATE OF CORRECTION

PATENT NO. : 9,974,815 B2
APPLICATION NO. : 15/803723
DATED : May 22, 2018
INVENTOR(S) : Imke Elisabeth Mulder et al.

It is certified that error appears in the above-identified patent and that said Letters Patent is hereby corrected as shown below:

On the Title Page

ITEM (72), INVENTORS, LINE 4:
"Seanin Marie McClusky, Aberdeen (GB)" should read --"Seanin Marie McCluskey, Aberdeen (GB)"--

Signed and Sealed this
Twentieth Day of November, 2018

Andrei Iancu
*Director of the United States Patent and Trademark Office*

UNITED STATES PATENT AND TRADEMARK OFFICE
CERTIFICATE OF CORRECTION

PATENT NO. : 9,974,815 B2  
APPLICATION NO. : 15/803723  
DATED : May 22, 2018  
INVENTOR(S) : Mulder et al.

Page 1 of 1

It is certified that error appears in the above-identified patent and that said Letters Patent is hereby corrected as shown below:

On the Title Page

In Item (62) Related U.S. Application Data:
"Division of application No. 15/357,850, filed on Nov. 21, 2016, now Pat. No. 9,839,558."
Should read:
--Division of application No. 15/357,850, filed on Nov. 21, 2016, now Pat. No. 9,839,655.--

Signed and Sealed this
Twenty-fourth Day of November, 2020

Andrei Iancu
*Director of the United States Patent and Trademark Office*